United States Patent
Konishi

(10) Patent No.: US 7,413,541 B2
(45) Date of Patent: Aug. 19, 2008

(54) SURGERY SUPPORT SYSTEM FOR ENDOSCOPIC SURGERY

(75) Inventor: Sumihito Konishi, Mitaka (JP)

(73) Assignee: Olympus Corporation, Tokyo (JP)

( * ) Notice: Subject to any disclaimer, the term of this patent is extended or adjusted under 35 U.S.C. 154(b) by 418 days.

(21) Appl. No.: 10/792,240

(22) Filed: Mar. 3, 2004

(65) Prior Publication Data
US 2005/0054896 A1 Mar. 10, 2005

(30) Foreign Application Priority Data
Mar. 7, 2003 (JP) ............................ 2003-062049

(51) Int. Cl.
*A61B 1/00* (2006.01)
*A61B 1/04* (2006.01)
(52) U.S. Cl. ...................... 600/101; 600/118
(58) Field of Classification Search ................. 600/101, 600/109, 118, 160
See application file for complete search history.

(56) References Cited

U.S. PATENT DOCUMENTS

| | | | |
|---|---|---|---|
| 5,400,792 A | 3/1995 | Hoebel et al. | |
| 5,701,904 A * | 12/1997 | Simmons et al. | 600/301 |
| 5,785,652 A * | 7/1998 | Oka | 600/342 |
| 5,797,838 A * | 8/1998 | Oka | 600/300 |
| 5,894,322 A * | 4/1999 | Hamano et al. | 348/68 |
| 6,114,370 A * | 9/2000 | Wall, Jr. | 514/410 |
| 2004/0044269 A1* | 3/2004 | Shibata | 600/101 |
| 2004/0153443 A1* | 8/2004 | McDonald et al. | 707/3 |

FOREIGN PATENT DOCUMENTS

JP    2000-276540    10/2000

* cited by examiner

*Primary Examiner*—John P. Leubecker
*Assistant Examiner*—Philip R Smith
(74) *Attorney, Agent, or Firm*—Scully, Scott, Murphy & Presser, P.C.

(57) ABSTRACT

An endoscopic surgical system has, in a hospital, multiple operating rooms A to J having anesthesia-apparatus related systems. Each of the anesthesia-apparatus related systems is connected to a hospital network managed by a server through a communication circuit. The anesthesia-apparatus related system is connected to an endoscopic system through a cable so as to communicate with each other interactively.

16 Claims, 18 Drawing Sheets

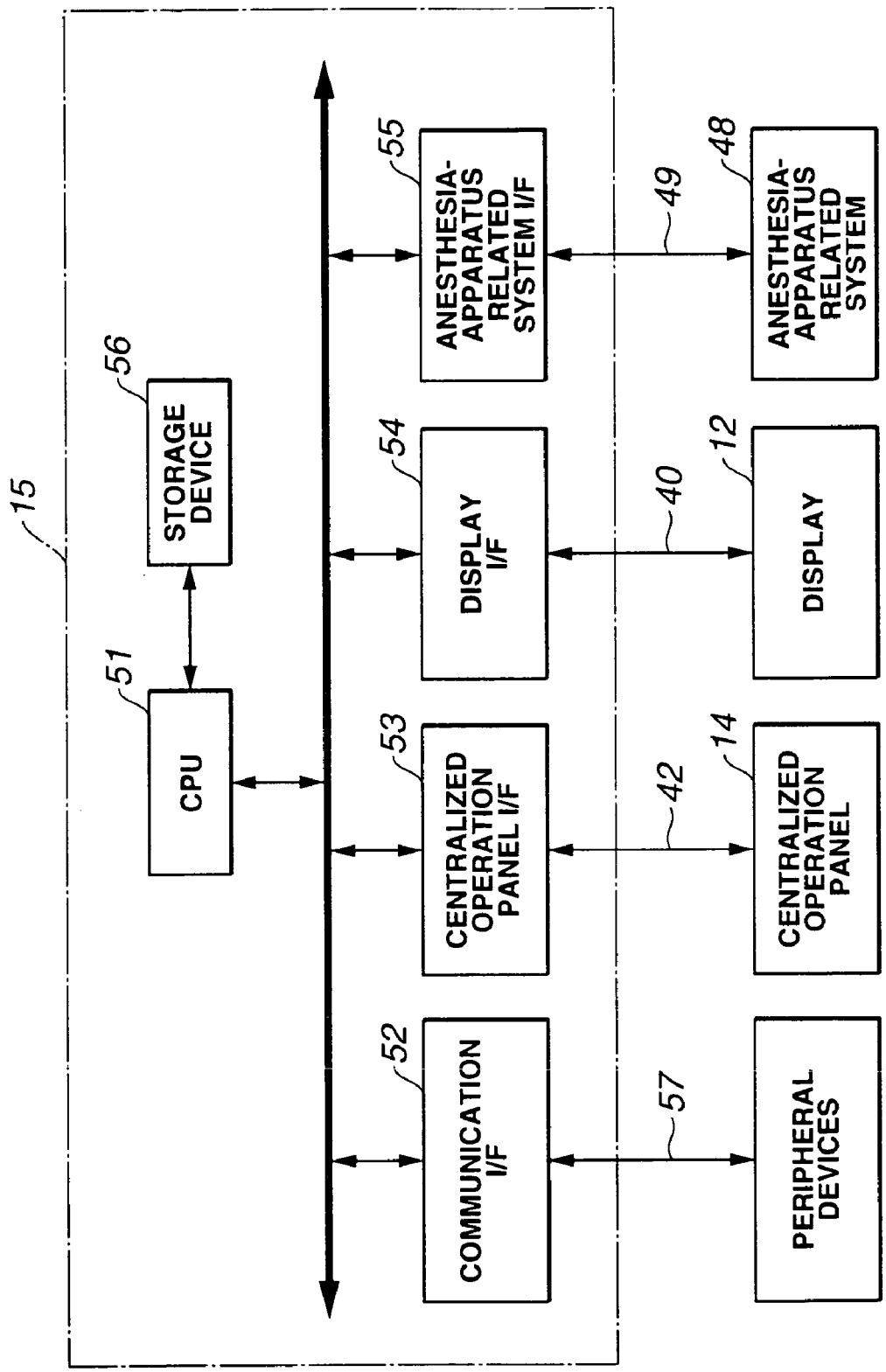

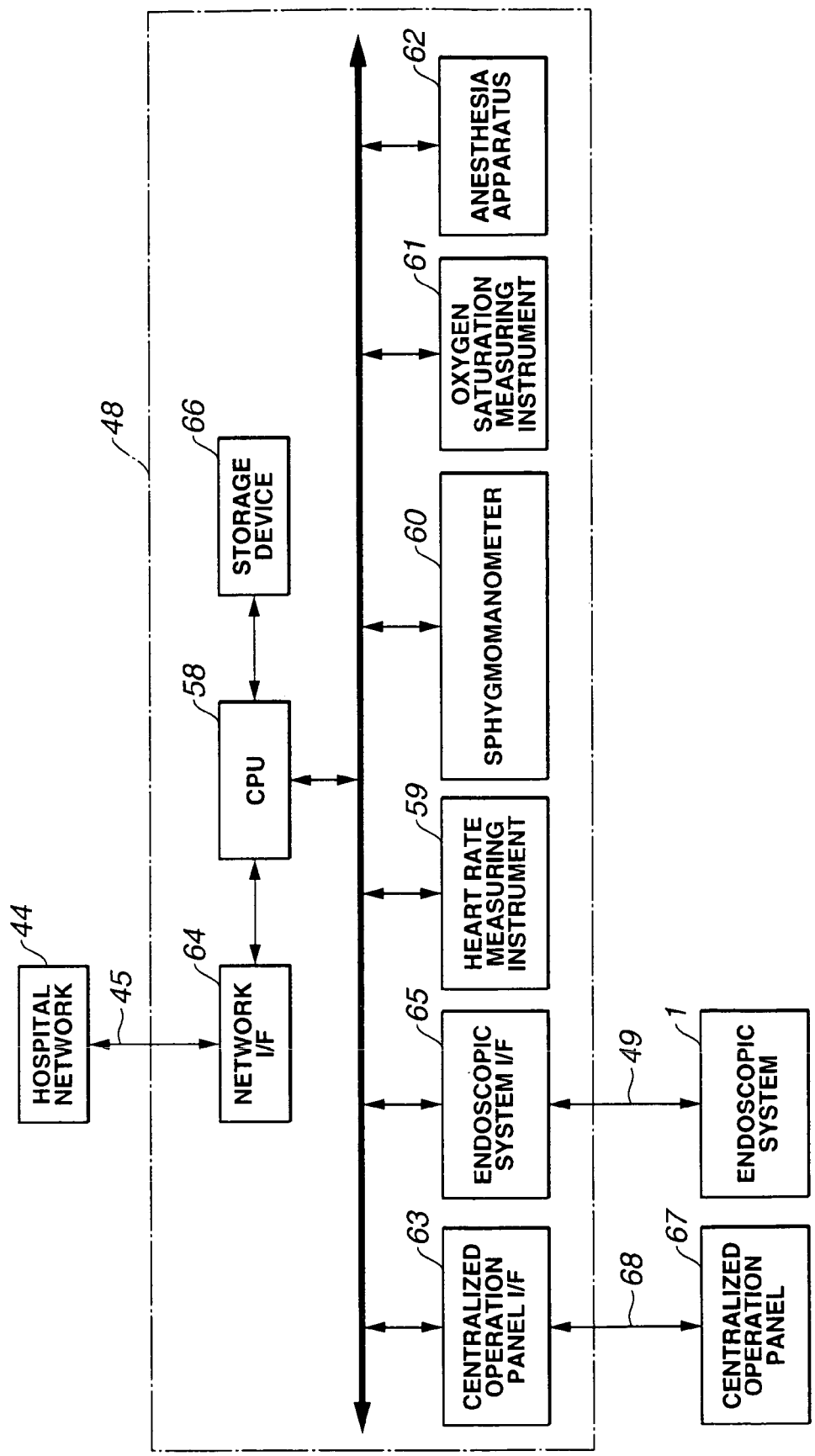

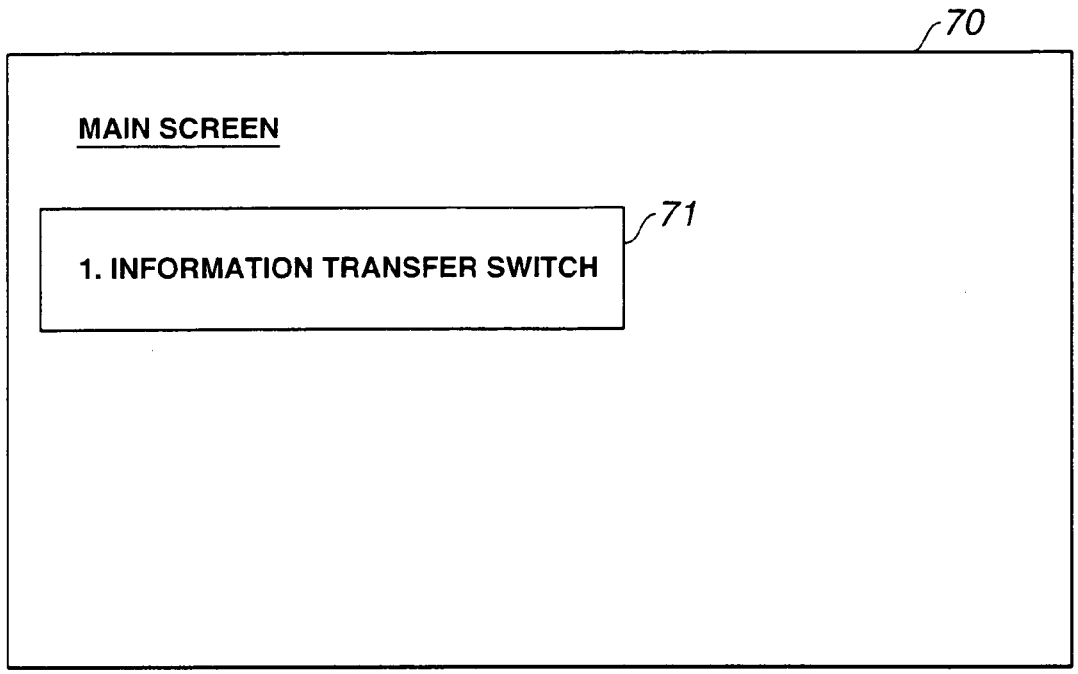
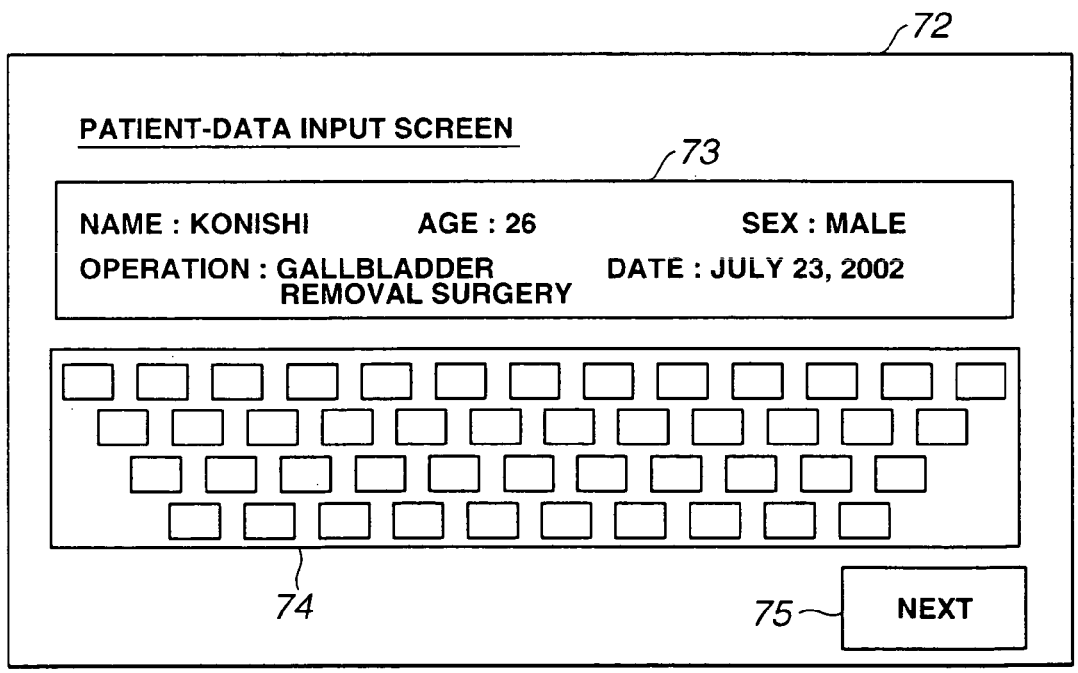

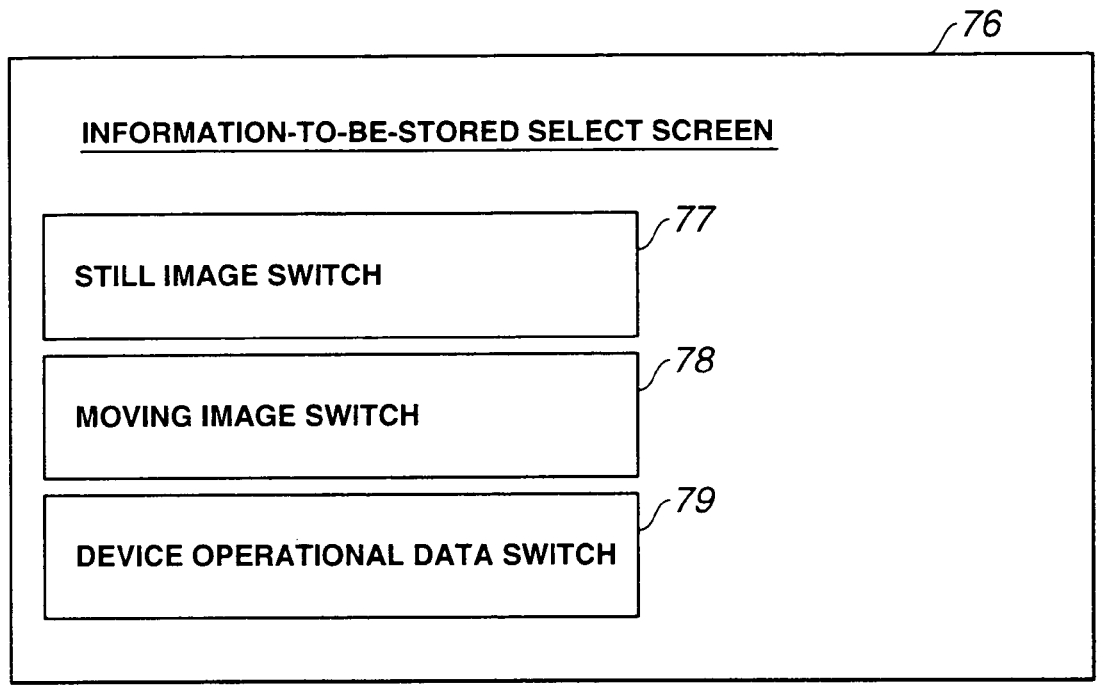
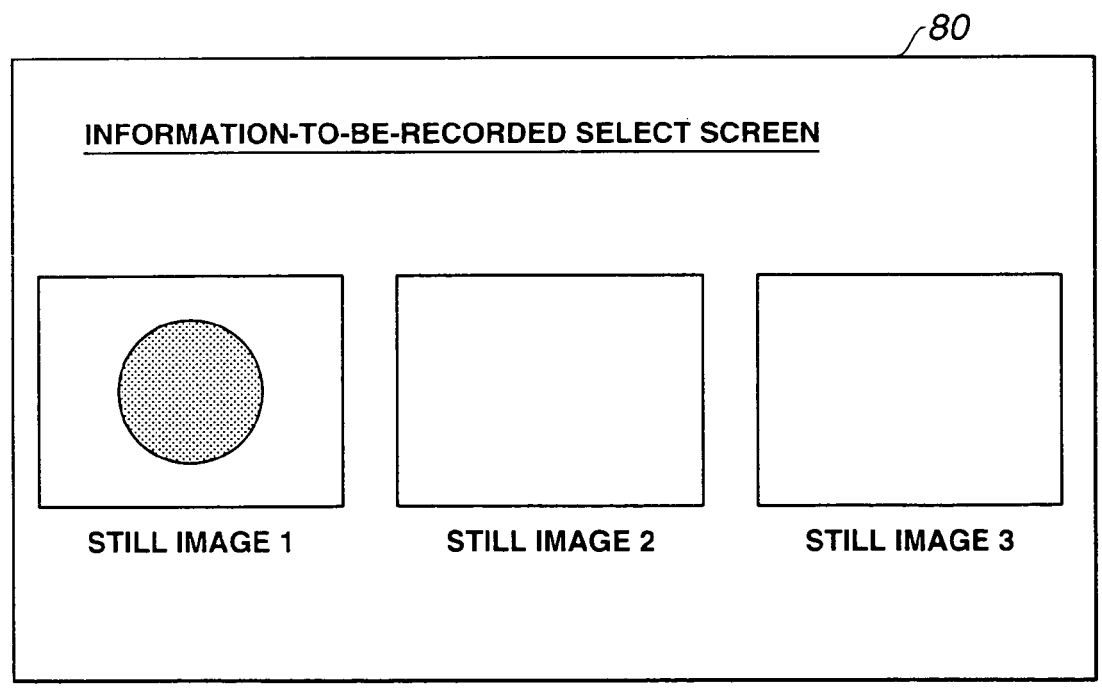

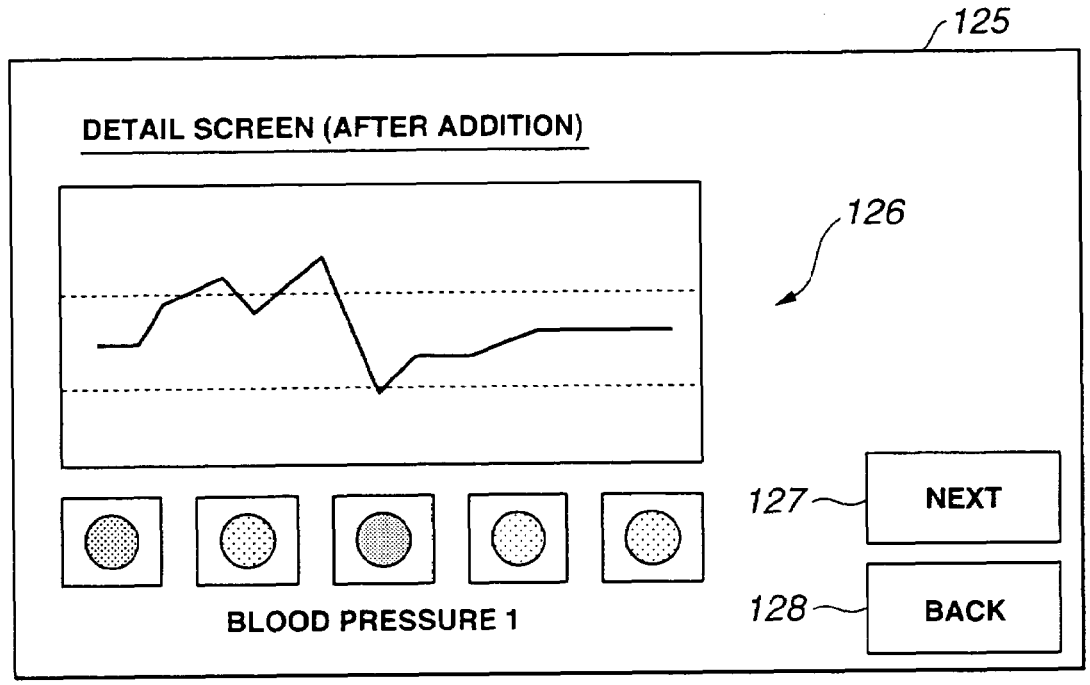
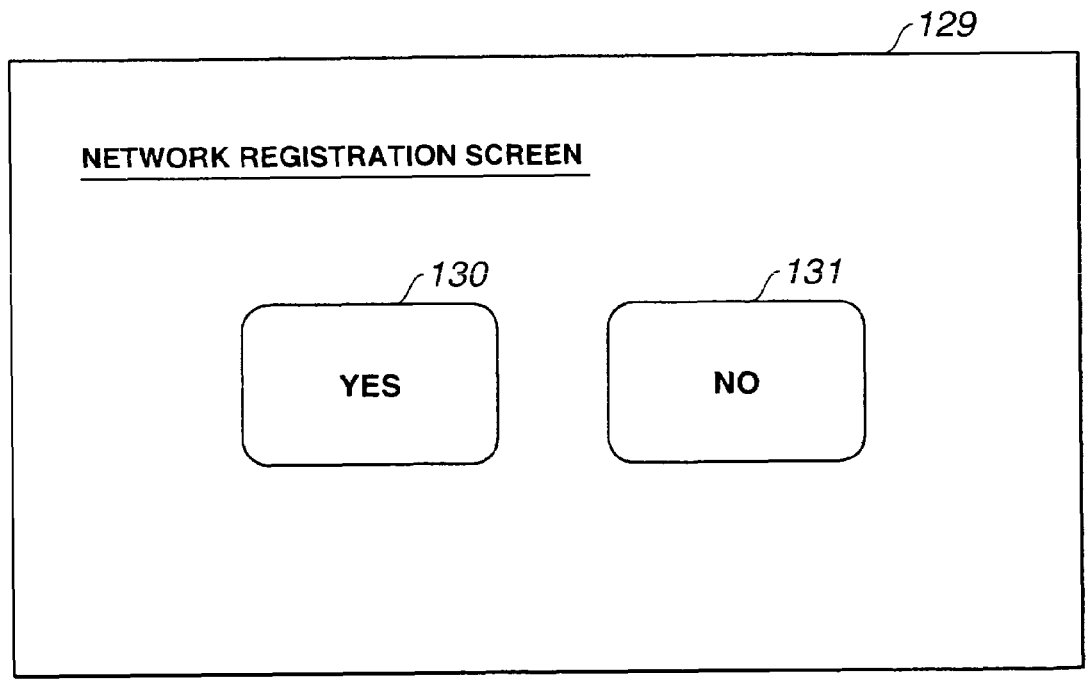

SURGERY SUPPORT SYSTEM FOR ENDOSCOPIC SURGERY

This application claims benefit of Japanese Applications No. 2003-62049 filed in Japan on Mar. 7, 2003, the contents of which are incorporated by this reference.

BACKGROUND OF THE INVENTION

1. Field of the Invention

The present invention relates to an endoscopic surgical system for remotely supporting surgery.

2. Related Art Statement

Recently, an endoscopic apparatus is widely used. The endoscopic apparatus may be used for observing organs within a body cavity by inserting a long and narrow insert portion into the body cavity and/or for performing different kinds of treatments and procedures by using a treating device being inserted into a treating-device insert channel as needed.

An endoscopic surgical system using the endoscope is used in an equipment system having various data/images in an operating room.

For example, according to a conventional technology as disclosed in Japanese Laid-Open Patent Publication No. 2000-276540, information such as medical treatment information of patients and operational information for endoscopic image surgical apparatus can be stored.

In such a conventional endoscopic surgical system, anesthesia-related apparatus and endoscope-related apparatus need to hold a large amount of data and become more complicated. In the conventional endoscopic surgical system, an anesthesia-related apparatus and an endoscope-related apparatus are connected to a network separately and may transfer, for example, data independently.

SUMMARY OF THE INVENTION

An endoscopic surgical system according to the present invention includes an endoscopic system provided in an operating room and usable with an anesthesia-apparatus related system connected to a predetermined communication circuit, a transceiver provided in the anesthesia-apparatus related system, which can send and receive information, and an information creating portion for creating third information by associating first information sent from the anesthesia-apparatus related system through the transceiver and second information detected in the endoscopic system with a same patient.

An endoscopic surgical system according to the present invention includes an anesthesia-apparatus related system having an anesthesia information recording portion for chronologically and sequentially recording anesthesia-related information relating to anesthesia in an operation, an endoscopic system having an image recording portion for chronologically and sequentially recording operated-part image information of a patient, a communication portion for communicating between the anesthesia-apparatus related system and the endoscopic system, an image-read-out control portion provided in the endoscopic system for reading out and outputting to the communication portion the operated-part image information recorded in the image recording portion based on time information communicated from the anesthesia-apparatus related system to the endoscopic system by the communication portion, and a recording control portion provided in the anesthesia-apparatus related system for controlling the anesthesia information recording portion to record the operated-part image information sent from the endoscopic system to the anesthesia-apparatus related system through the communication portion under the control of the image-read-out control portion in connection with the anesthesia-related information of a same patient.

An endoscopic surgical system according to the present invention includes an information transfer select portion for selecting whether or not information of an anesthesia-apparatus related system is transferred to a recording device provided in a server connecting to a hospital network, an information-to-be-recorded select portion for selecting whether or not information of the anesthesia-apparatus related system is added to the recording device of the server connecting to the hospital network, an information-to-be-recorded checking portion for checking the information of the anesthesia-apparatus related system, which is selected in the information-to-be-recorded select portion, and an information-to-be-recorded adding portion for registering the information of the anesthesia-apparatus related system, which is checked in the information-to-be-recorded checking portion, with the recording device of the server connected to the hospital network.

An endoscopic surgical system according to the present invention includes an upper limit value/lower limit value input portion for receiving inputs of an upper limit value and lower limit value of information of an anesthesia-apparatus related system, an abnormality detecting portion for detecting an abnormality of the anesthesia-apparatus related system based on the upper limit value and lower limit value, which are input in the upper limit value/lower limit value input portion, a function-to-be-linked select portion for, when an abnormality of the anesthesia-apparatus related system is detected by the abnormality detecting portion, selecting a function in the endoscopic system to be recorded in connection with the abnormality of the anesthesia-apparatus related system, an abnormality recording portion for implementing the function in the endoscopic system, which is selected in the function-to-be-linked select portion, and for recording the abnormality of the anesthesia-apparatus related system, and a filing portion for filing the information before and after the detection of the abnormality, which is recorded by the abnormality recording portion.

BRIEF OF DESCRIPTION OF THE DRAWINGS

FIG. 4 is a block diagram showing a construction of a system controller in FIG. 3;

FIG. 5 is a block diagram showing a construction of an anesthesia-apparatus related system in FIG. 1;

FIG. 6 is a diagram showing a first operation screen to be displayed on a centralized operation panel of the anesthesia-apparatus related system in FIG. 1;

FIG. 7 is a diagram showing a second operation screen to be displayed on the centralized operation panel of the anesthesia-apparatus related system in FIG. 1;

FIG. 8 is a diagram showing a third operation screen to be displayed on the centralized operation panel of the anesthesia-apparatus related system in FIG. 1;

FIG. 9 is a diagram showing a fourth operation screen to be displayed on the centralized operation panel of the anesthesia-apparatus related system in FIG. 1;

FIG. 23 is a diagram showing a seventh operation screen to be displayed on the centralized operation panel of the anesthesia-apparatus related system in FIG. 16;

FIG. 24 is a diagram showing an eighth operation screen to be displayed on the centralized operation panel of the anesthesia-apparatus related system in FIG. 16;

Figure 16:
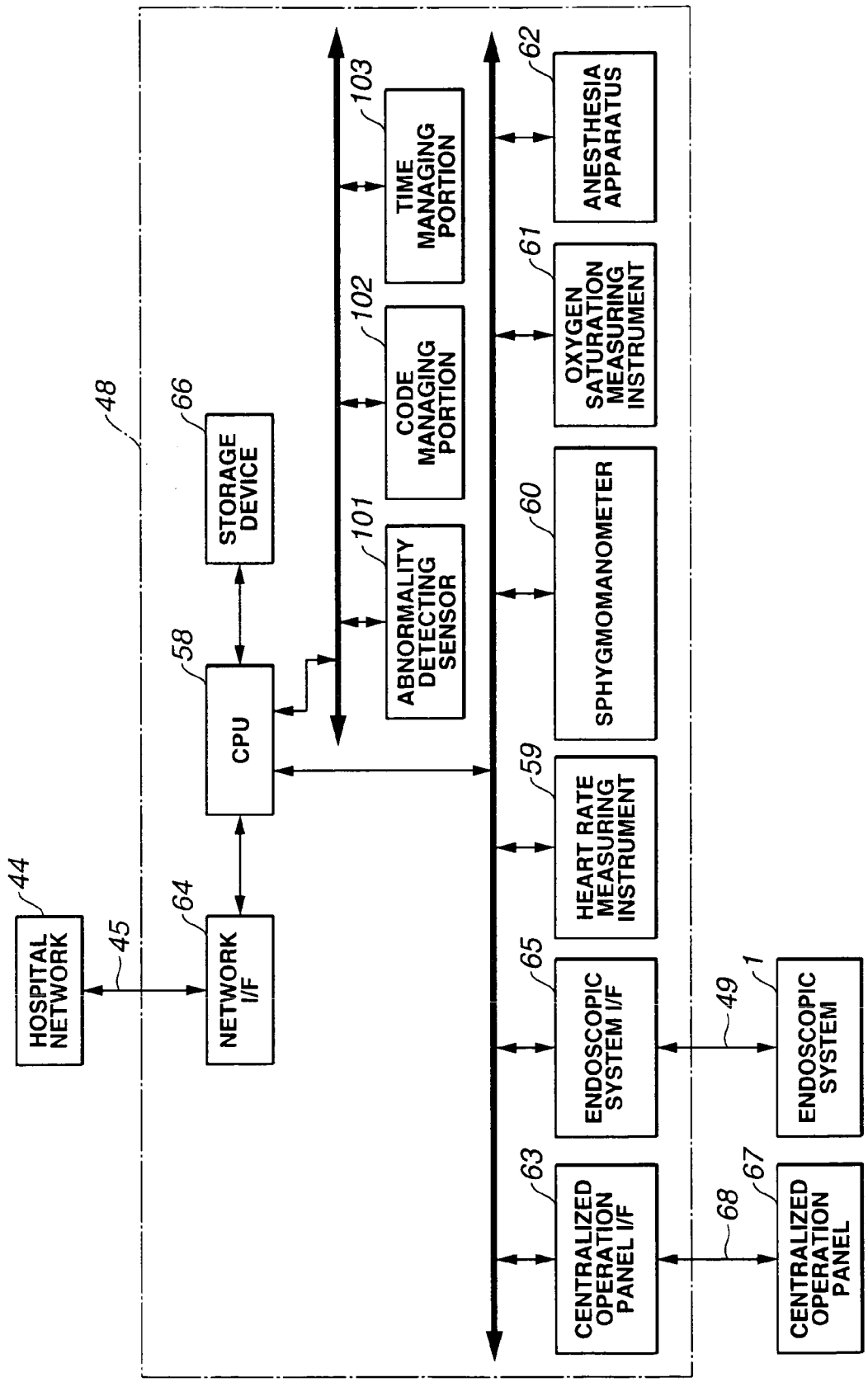
FIG. 16 is a block diagram showing a construction of an anesthesia-apparatus related system to be connected to the system controller in FIG. 15.
Figure 25:
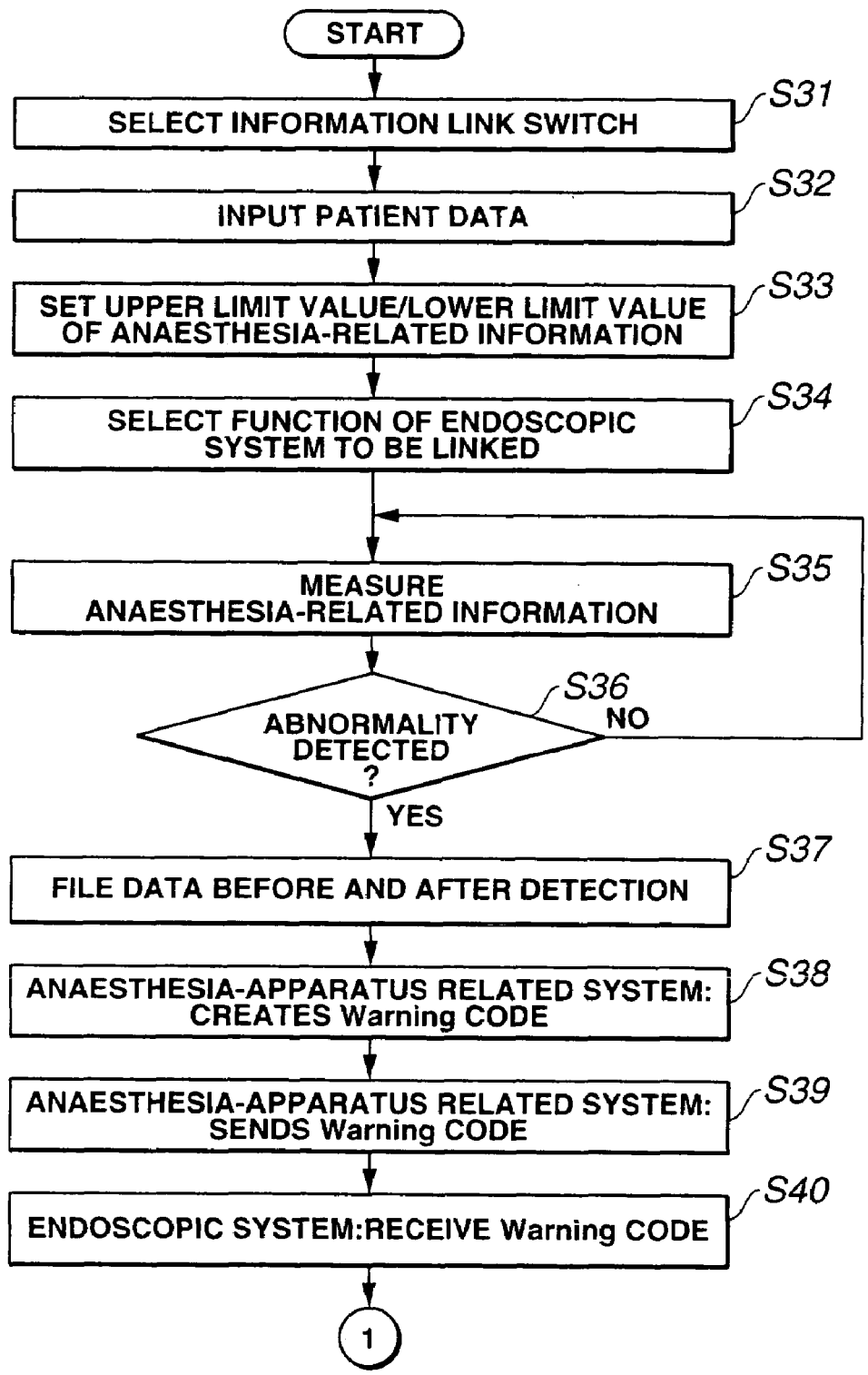
Figure 26:
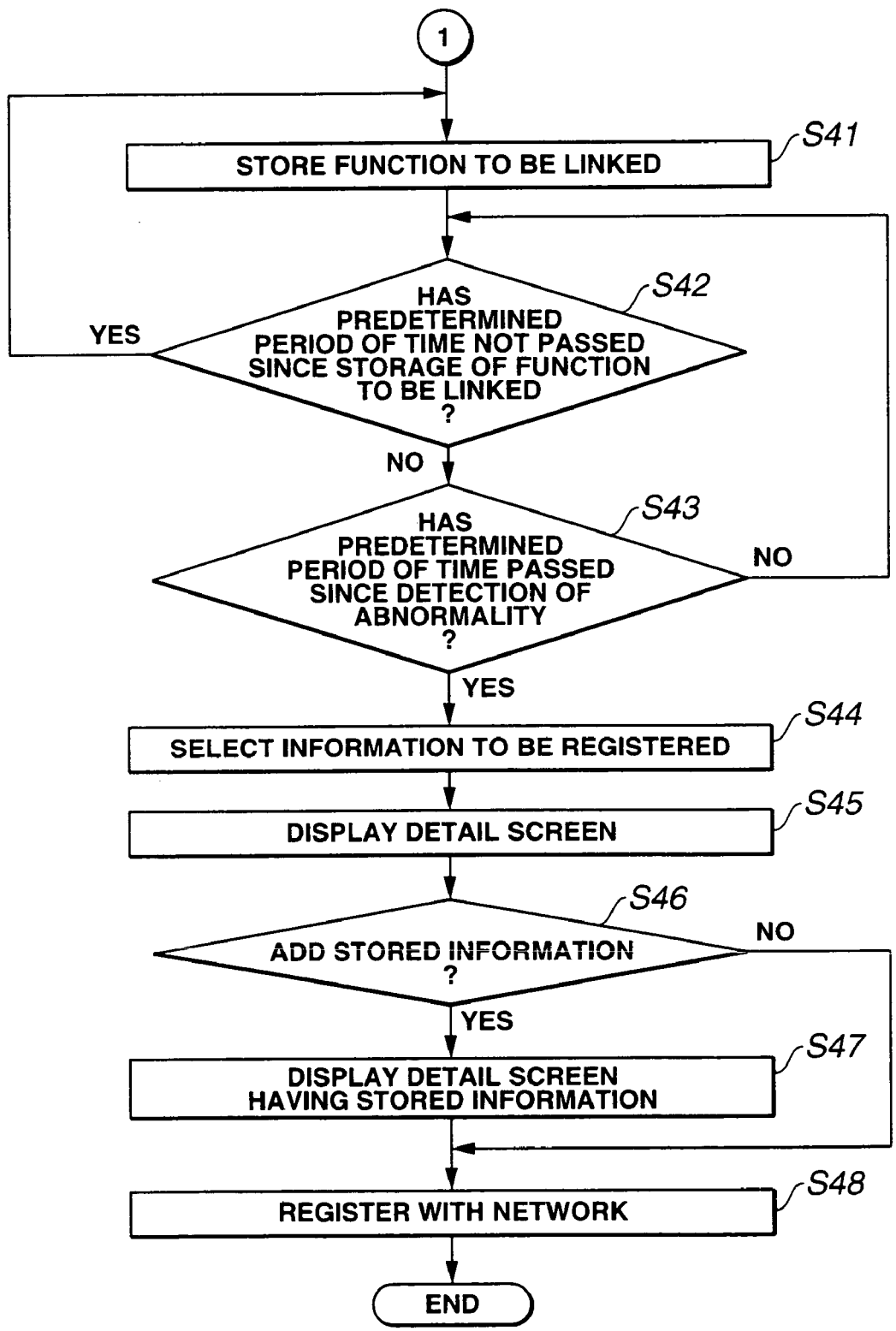

FIG. 25 is a first flowchart showing a method for associating and storing, in a hospital network, data indicating an abnormal value and data held in the endoscopic system at that time when information in the anesthesia-apparatus related system in FIG. 16 indicates the abnormal value; and FIG. 26 is a second flowchart showing a method for associating and storing, in a hospital network, data indicating an abnormal value and data held in the endoscopic system at that time when information in the anesthesia-apparatus related system in FIG. 16 indicates the abnormal value.

DETAILED DESCRIPTION OF PREFERRED EMBODIMENTS

Embodiments of the present invention will be described below with reference to drawings.

[First Embodiment]

Figure 1:
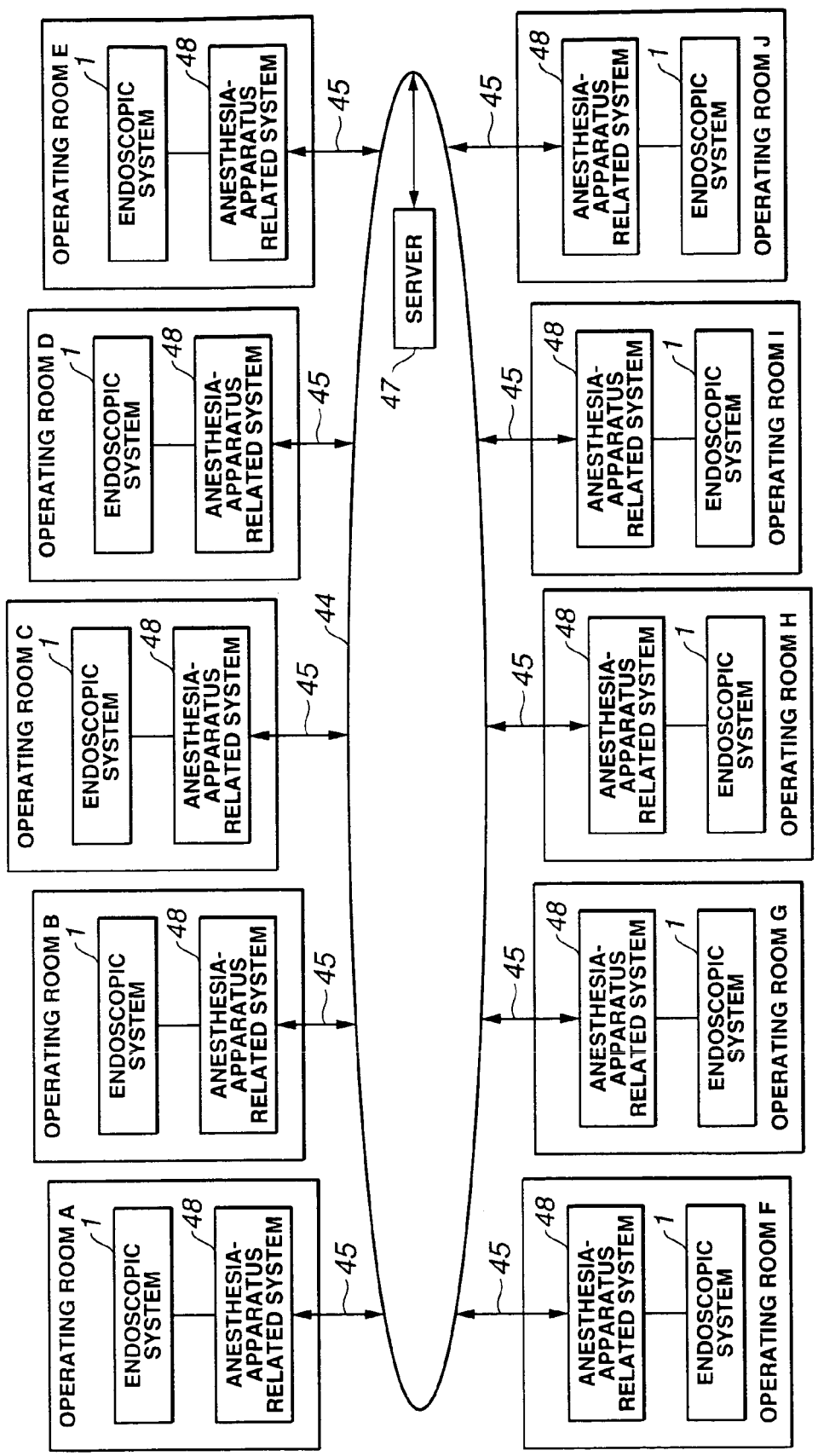
FIG. 1 is a construction diagram showing a construction of an endoscopic surgical system according to a first embodiment of the present invention.

According to an endoscopic surgical system of this embodiment, as shown in FIG. 1, a hospital has multiple operating rooms A to J each provided with an anesthesia-apparatus related system 48.

The anesthesia-apparatus related system 48 is connected to a hospital network 44 managed by a server 47 through a communication circuit 45 such as a LAN cable. The anesthesia-apparatus related system 48 is also connected to an endoscopic system 1 through a cable, not shown. The anesthesia-apparatus related system 48 can interactively communicate with the endoscopic system 1. The server 47 includes a recording device, not shown.

Figure 2:
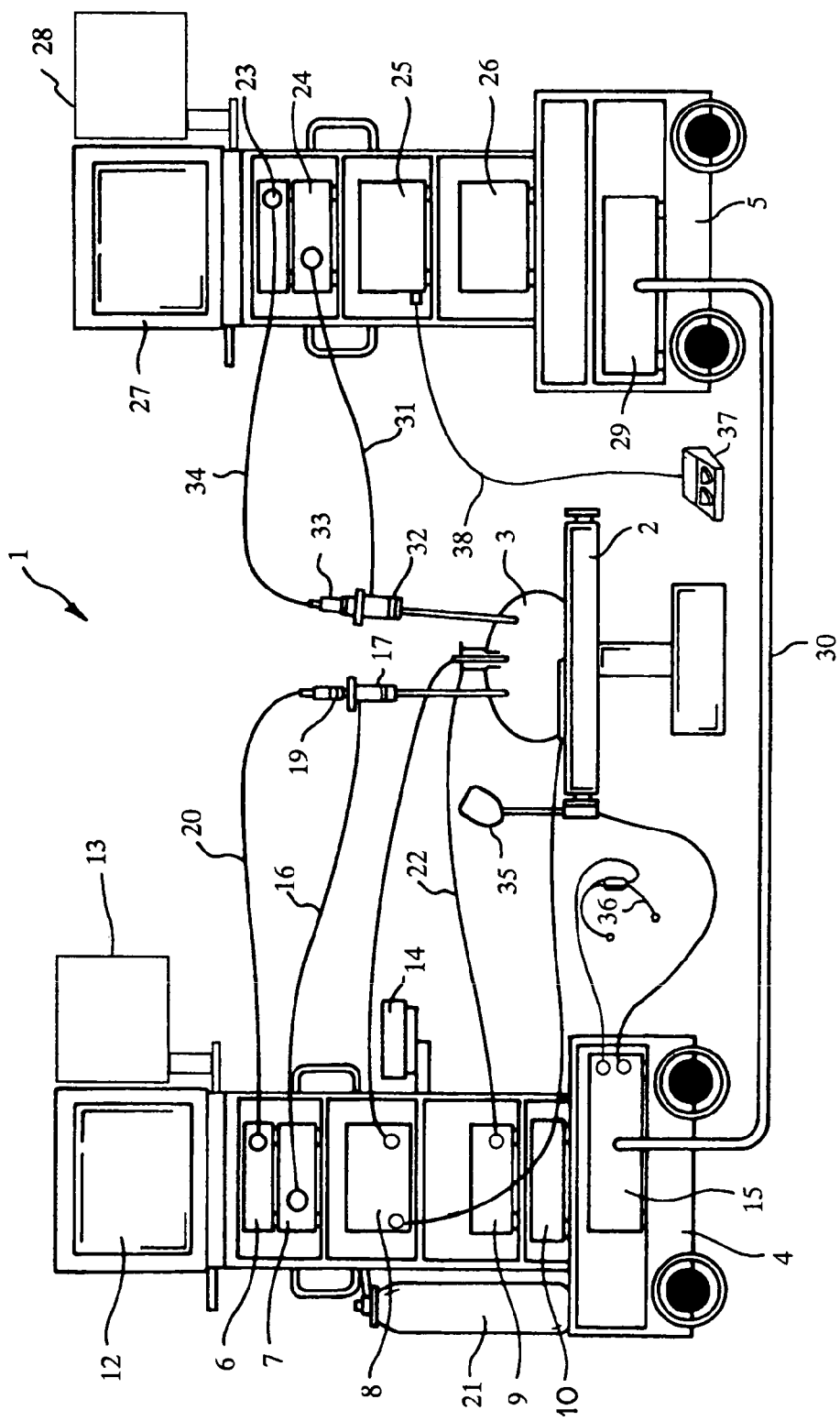
FIG. 2 is a construction diagram showing a construction of the endoscopic system in FIG. 1.

As shown in FIG. 2, the endoscopic system 1 has a first trolley 4 and a second trolley 5 on both sides of an operating table 2 on which a patient 3 lies down. Multiple endoscope peripheral apparatus for performing observation, tests, treatments, recording and so on are placed on these trolleys 4 and 5.

The first trolley 4 includes a first TV camera device 6, a first light source device 7, a high frequency cauterizing device (called electric surgical knife hereinafter) 8, a pneumoperitoneum apparatus 9, a video printer 10, a first display 12, a centralized operation panel 14 and a system controller 15 and the like. The centralized operation panel 14 is positioned in an unsterilized area so that a nurse can concentrate upon operating medical equipment. The centralized operation panel 14 has a pointing device, not shown, such as a mouse and a touch panel.

The devices including the first TV camera device 6, the first light source device 7, the high-frequency cauterizing device (called electric surgical knife, hereinafter) 8, the pneumoperitoneum apparatus 9, the video printer 10, the first display 12, the centralized operation panel 14 and the like are connected to the system controller 15 through a cable, which will be described later. The apparatus including the first TV camera device 6, the first light source device 7, the high-frequency cauterizing device (called electric surgical knife, hereinafter) 8, the pneumoperitoneum apparatus 9, the video printer 10, the first display 12, the centralized operation panel 14 and the system controller 15 and the like can communicate with the system controller 15 interactively.

The first light source device 7 is connected to a first endoscope 17 through a light-guide cable 16 for transmitting illumination light. The first light source device 7 is arranged to supply illumination light to a light guide of the first endoscope 17.

The first endoscope 17 has an insert portion to be inserted into the abdominal region of the patient 3. The illumination light from the first light source device 7 illuminates an affected part within the abdominal region of the patient 3.

The first endoscope 17 captures reflected light from the illuminated affected part, for example, within the abdominal region of the patient 3 by using an observation optical device and transmits the captured light as an endoscopic image to an eyepiece.

A first camera head 19 including an imaging element is attached to an eyepiece of the first endoscope 17. The first camera head 19 picks up an endoscopic image supplied from the eyepiece of the first endoscope 17 by using incorporated the imaging element, not shown, and outputs imaging signals.

The imaging signals from the first camera head 19 are transmitted to the first TV camera device 6 through a camera cable 20. The first TV camera device 6 generates video signals by processing the received imaging signals in a signal processing circuit, not shown. The first TV camera device 6 outputs the video signals to the first display 12 through the system controller 15 and can display the endoscopic image of the affected part, for example.

The system controller 15 includes an external-media recording device, not shown. The system controller 15 can thus output to the first display 12 and display thereon image data recorded in an external recording medium.

The system controller 15 is also connected to a communication circuit 45 provided in a hospital, not shown, through a cable, not shown. The system controller 15 can thus output to the first display 12 and display thereon image data, for example, recorded in a recording device of the server 47 connecting to the communication circuit 45.

A CO2 cylinder 21 is connected to the pneumoperitoneum apparatus 9. Thus, the pneumoperitoneum apparatus 9 can supply CO2 gas into the abdominal region of the patient 3 through a pneumoperitoneum tube 22 extending from the pneumoperitoneum apparatus 9 to the patient 3.

The second trolley 5 includes a second TV camera device 23, a second light source device 24, an ultrasonic processing device 25, a VTR 26, a second display 27, a centralized display panel 28 and a relay unit 29 and the like. The devices including the second TV camera device 23, the second light source device 24, the ultrasonic processing device 25, the VTR 26, the second display 27, the centralized display panel 28 and the like are connected to the relay unit 29 through a cable, not shown, and can interactively communicate with the relay unit 29.

The second light source device 24 is connected to a second endoscope 32 through a light-guide cable 31 for transmitting illumination light. The second light source device 24 is arranged to supply illumination light to a light guide of the second endoscope 32.

The second endoscope 32 has an insert portion to be inserted into the abdominal region of the patient 3. The illumination light from the second light source device 24 illuminates an affected part within the abdominal region of the patient 3.

The second endoscope 32 captures light reflected from the illuminated affected part, for example, within the abdominal region of the patient 3 by using an observation optical device and transmits the captured light as an endoscopic image to an eyepiece.

A second camera head 33 including an imaging element is attached to the eyepiece of the second endoscope 32. The second camera head 33 picks up an endoscopic image supplied from the eyepiece of the second endoscope 32, by using the incorporated imaging element, not shown, and outputs imaging signals.

The imaging signals from the second camera head 33 are transmitted to the second TV camera device 23 through a camera cable 34. The second TV camera device 23 generates video signals by processing the received imaging signals in a signal processing circuit, not shown. The second TV camera device 23 outputs the video signals to the second display 27 through the relay unit 29 and can display the endoscopic image of the affected part, for example.

The system controller 15 and the relay unit 29 are connected through a system cable 30. A Dr. remote controller (hereinafter, referred to as Dr. remote control) 35 to be used by an operator for manipulating equipment from an unsterilized area is also connected to the system controller 15.

Furthermore, a microphone 36 can be connected to the system controller 15. The system controller 15 recognizes the voice input from the microphone 36 and can control devices through the voice of an operator.

A foot-switch 37 is connected to the ultrasonic processing device 25 through a cable 38.

Figure 3:
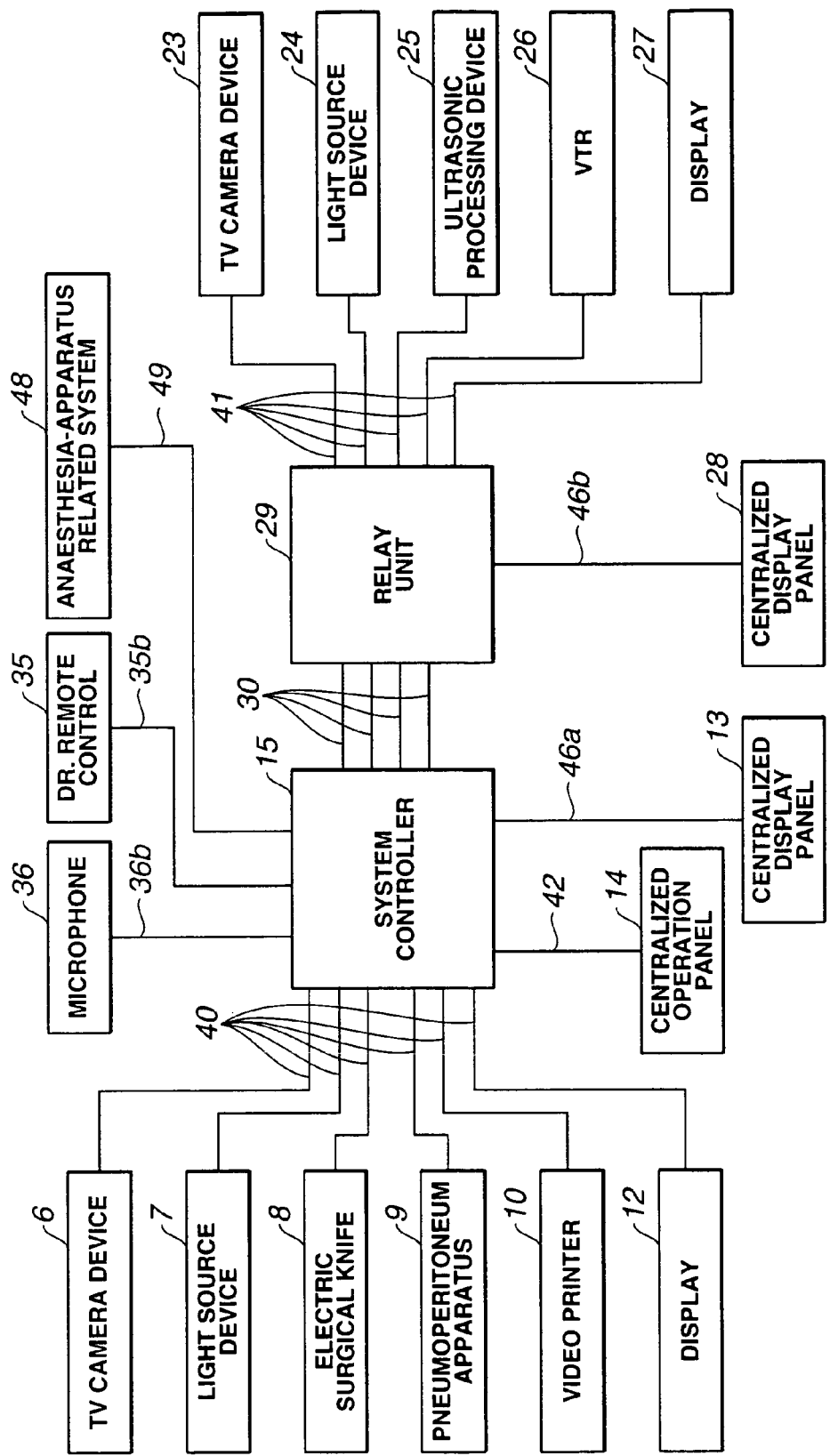
FIG. 3 is a block diagram showing a connection configuration of the endoscopic system in FIG. 2.

As shown in FIG. 3, the centralized operation panel 14, the first TV camera device 6, the first light source device 7, the electric surgical knife 8, the pneumoperitoneum apparatus 9, the video printer 10 and the first display 12 are connected to the system controller 15 through a communication cable 40 and can exchange data and video signals with the system controller 15.

The second TV camera device 23, the second light source device 24, the ultrasonic processing device 25, the VTR 26 and the second display 27 are connected to the relay unit 29 through the communication cable 41 and can exchange data and video signals with the relay unit 29.

The relay unit 29 is also connected to the system controller 15 through the system cable 30 (see FIG. 2).

The centralized operation panel 14 is connected to the system controller 15 through a centralized operation panel cable 42. The microphone 36 is connected to the system controller 15 through a headset cable 36*b*. The Dr. remote control 35 is connected to the system controller 15 through a remote-control cable 35*b*.

The centralized display panel 13 is connected to the system controller 15 through a system cable 46*a*. The centralized display panel 28 is also connected to the system controller 15 through a system cable 46*b*. The anesthesia-apparatus related system 48 is further connected to the system controller 15 through a system cable 49.

FIG. 4 shows an internal construction of the system controller 15.

The system controller 15 provided in an operating room includes a CPU 51, a communication interface (abbreviated to I/F, hereinafter) 52, a centralized operation panel I/F 53, a display I/F 54, an anesthesia-apparatus related system I/F 55 and a storage device 56.

The system controller 15 is connected to the medical devices through a communication cable 57 by using the communication I/F 52. The system controller 15 is connected to the centralized operation panel 14 through the centralized operation panel cable 42 by using the centralized operation panel I/F 53. The system controller 15 is connected to the display 12 through the communication cable 40 by using the display I/F 54. The system controller 15 is connected to the anesthesia-apparatus related system 48 through the system cable 49 by using the anesthesia-apparatus related system I/F 55.

The I/Fs 34 to. 37 and the storage device 56 are connected to the CPU 51 and are centrally controlled by the CPU 51.

FIG. 5 shows an internal construction of the anesthesia-apparatus related system 48.

The anesthesia-apparatus related system 48 provided in an operating room includes a CPU 58, a heart rate measuring instrument 59, a sphygmomanometer 60, an oxygen saturation measuring instrument 61, an anesthesia device 62, a centralized operation panel I/F 63, a network I/F 64, an endoscopic system I/F 65 and a storage device 66.

The anesthesia-apparatus related system 48 is connected to the endoscopic system 1 through the system cable 49 by using the endoscopic system I/F 65. The anesthesia-apparatus related system 48 is connected to the hospital network 44 through the communication circuit 45 by using the network I/F 64.

The centralized operation panel I/F 63, the network I/F 64, the heart rate measuring instrument 59, the sphygmomanometer 60, the oxygen saturation measuring instrument 61, the anesthesia device 62 and the storage device 66 are connected to the CPU 58 and are centrally controlled by the CPU 58.

In other words, the network I/F 64 and the endoscopic system I/F 65 are included in a transceiver while the CPU 58 is included in an information generating portion.

FIGS. 6 to 13 show different kinds of operation screens on a centralized operation panel 67 of the anesthesia-apparatus related system 48.

FIG. 6 shows a main screen 70. The main screen 70 has an information transfer switch 71. When the information transfer switch 71 is selected on the main screen 70 on the centralized operation panel 67, the main screen 70 is switched to a patient-data input screen 72 shown in FIG. 7. That is, the centralized operation panel 67 displays the patient-data input screen 72.

FIG. 7 shows the patient-data input screen 72. The patient-data input screen 72 has a patient-data input field 73, a keyboard switch 74 and a NEXT switch 75. When patient data is input through the keyboard switch 74 and the NEXT switch 75 is selected on the patient-data input screen 72, the patient-data input screen 72 is switched to an information-to-be-recorded select screen 76 shown in FIG. 8. That is, the centralized operation panel 67 displays the information-to-be-recorded select screen 76.

FIG. 8 shows an information-to-be-recorded select screen 76. The information-to-be-recorded select screen 76 has a still image switch 77, a moving image switch 78 and a device operational data switch 79. When one of the switches is selected on the information-to-be-recorded select screen 76, the information-to-be-recorded select screen 76 is switched to the respective information-to-be-recorded select screen. That is, the centralized operation panel 67 displays the information-to-be-recorded select screen.

FIG. 9 shows an information-to-be-recorded select screen 80 for still images. The information-to-be-recorded select screen 80 displays a still image stored in the storage device 56 of the system controller 15. When a desired still image is selected on the information-to-be-recorded select screen 80, the information-to-be-recorded select screen 80 is switched to a still-image checking screen 81 shown in FIG. 10. That is, the centralized operation panel 67 displays the still-image checking screen 81.

Figure 10:
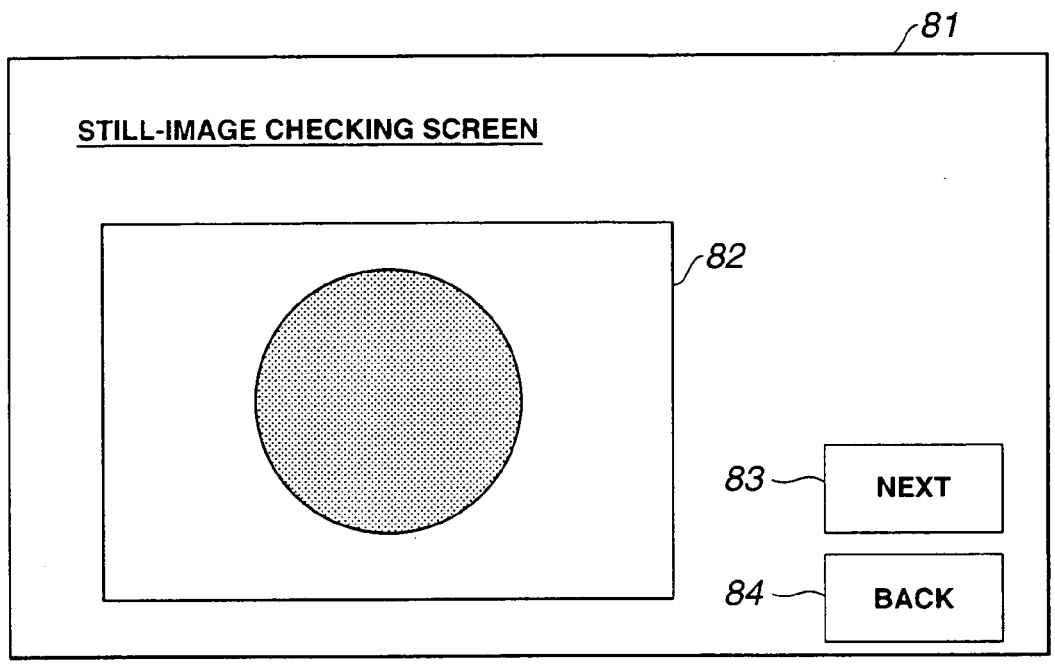
FIG. 10 is a diagram showing a fifth operation screen to be displayed on the centralized operation panel of the anesthesia-apparatus related system in FIG. 1.

FIG. 10 shows the still-image checking screen 81. The still-image checking screen 81 has a still-image display area 82, a NEXT switch 83 and a BACK switch 84. A still image selected on the information-to-be-recorded select screen 80 in FIG. 9 is enlarged and is displayed on the still-image display area 82.

Figure 11:
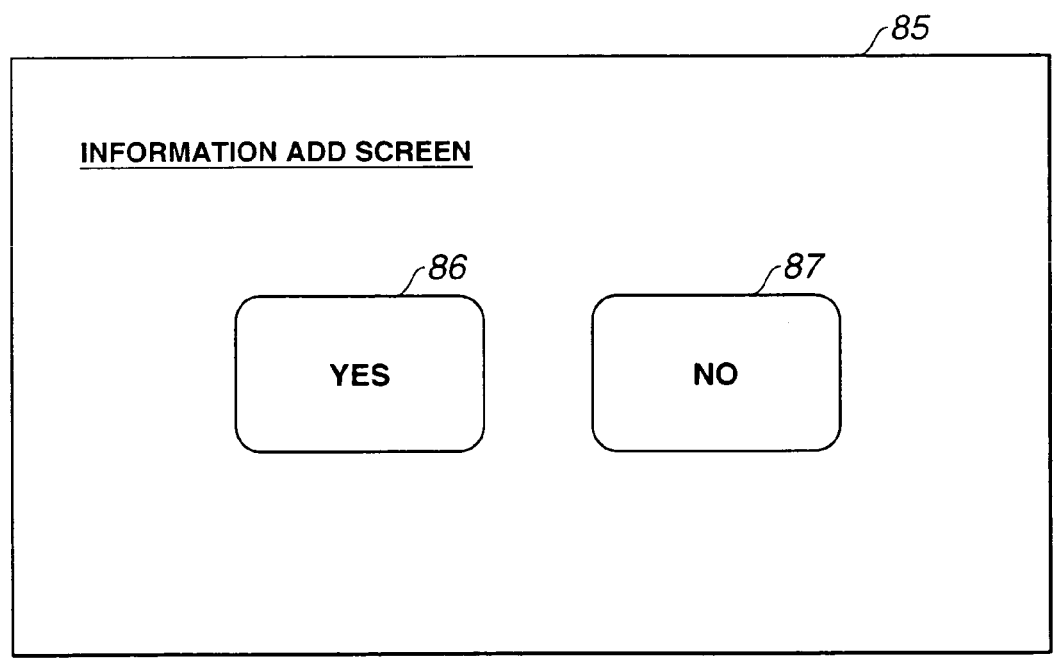
FIG. 11 is a diagram showing a sixth operation screen to be displayed on the centralized operation panel of the anesthesia-apparatus related system in FIG. 1.

When the NEXT switch 83 is selected on the still-image checking screen 81, the still-image checking screen 81 is switched to an information add screen 85 shown in FIG. 11. That is, the centralized operation panel 67 displays the information add screen 85. On the other hand, when the BACK switch 84 is selected on the still-image checking screen 81, the centralized operation panel 67 returns to the information-to-be-recorded select screen 80 in FIG. 9.

FIG. 11 shows the information add screen 85. The information add screen 85 is a screen for selecting whether data of the anesthesia-apparatus related system 48 is added to selected registered data or not. The information add screen 85 has an YES switch 86 and a NO switch 87.

Figure 12:
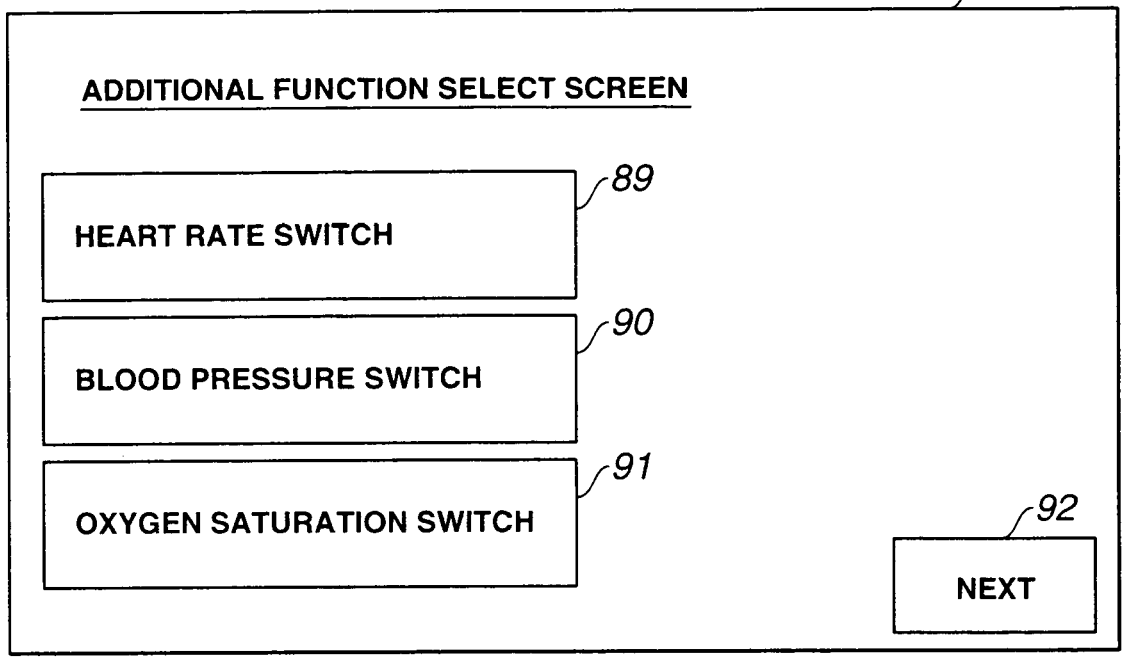
FIG. 12 is a diagram showing a seventh operation screen to be displayed on the centralized operation panel of the anesthesia-apparatus related system in FIG. 1.

When the YES switch 86 is selected on the information add screen 85, the information add screen 85 is switched to an additional function select screen 88 shown in FIG. 12. That is, the centralized operation panel 67 displays the additional function select screen 88.

When the NO switch 87 is selected on the information add screen 85 on the centralized operation panel 67, selected information is registered with a recording device of the server 47 through the anesthesia-apparatus related system 48 and the hospital network 44 (see FIG. 1).

FIG. 12 shows the additional function select screen 88. The additional function select screen 88 is a screen for adding data of the anesthesia-apparatus related system 48 to selected registered data. The additional function select screen 88 has a heart rate switch 89, a blood pressure switch 90, an oxygen saturation switch 91 and a NEXT switch 92.

Figure 13:
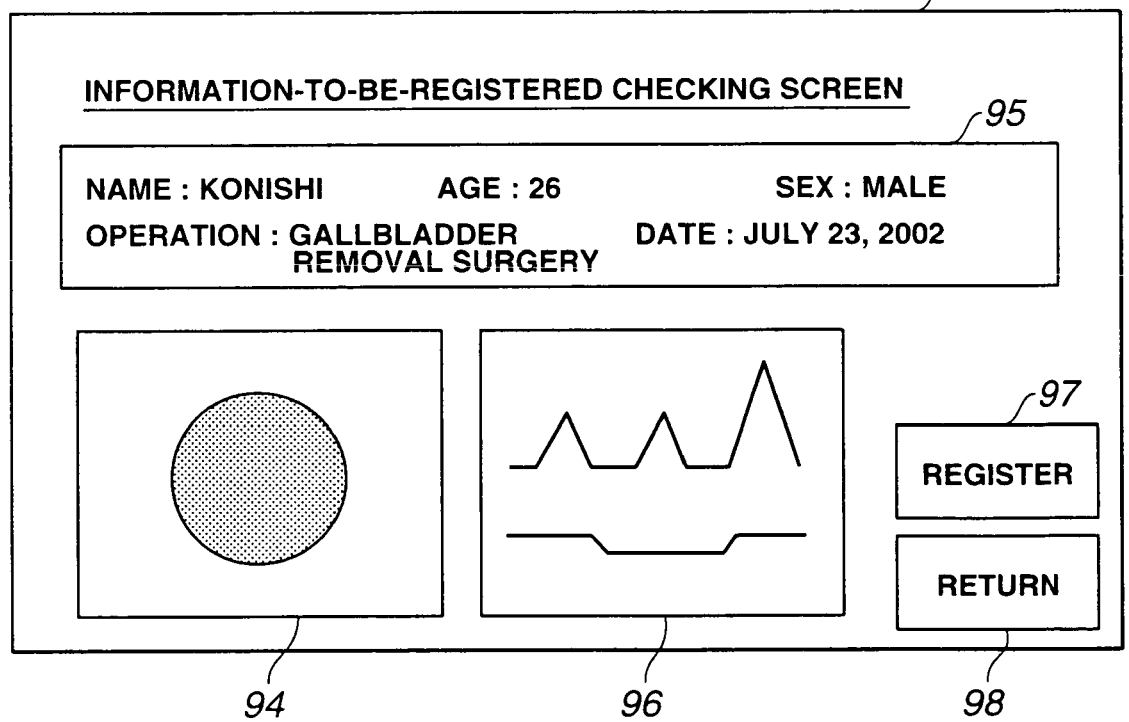
FIG. 13 is a diagram showing an eighth operation screen to be displayed on the centralized operation panel of the anesthesia-apparatus related system in FIG. 1.

When data to be added to registered information and then the NEXT switch 92 are selected on the additional function select screen 88, the centralized operation panel 67 displays an information-to-be-registered checking screen 93 shown in FIG. 13.

FIG. 13 shows the information-to-be-registered checking screen 93. The information-to-be-registered checking screen 93 has a recorded-information display area 94, a patient-data display area 95, a data display area 96 for the anesthesia-apparatus related system 48, a REGISTER switch 97 and a RETURN switch 98.

A still image to be registered is displayed on the recorded-information display area 94. Input patient data is displayed on the patient-data display area 95. Information on a selected function is displayed on the data display area 96.

When the REGISTER switch 97 is selected on the information-to-be-registered checking screen 93 on the centralized operation panel 67, data being displayed is stored in the recording device of the server 47 through the hospital network 44. When the RETURN switch 98 is selected on the information-to-be-registered checking screen 93, the centralized operation panel 67 displays the still-image checking screen 81 in FIG. 10 again.

Figure 14:
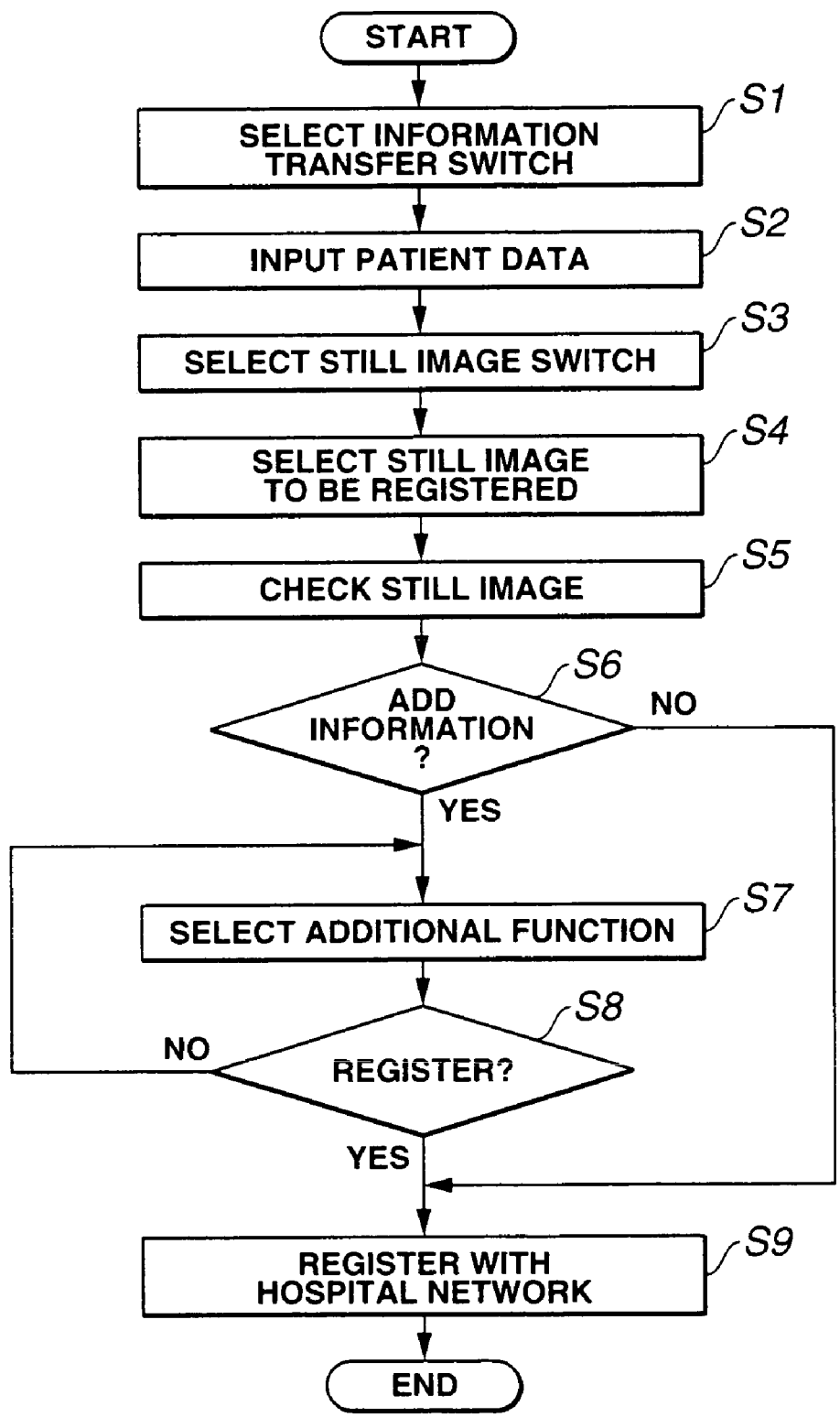
FIG. 14 is a flowchart showing a method for storing data held by the endoscopic system in FIG. 1 into a hospital network through the anesthesia-apparatus related system.

FIG. 14 is a flowchart showing a method for storing data held by the endoscopic system 1 into the hospital network 44 through the anesthesia-apparatus related system 48.

A method for recording and storing data held by the endoscopic system 1 into the recording device of the server 47 connected to the hospital network 44 through the anesthesia-apparatus related system 48 will be described with reference to FIG. 7.

At step S1, the CPU 58 of the anesthesia-apparatus related system 48 causes the centralized operation panel 67 to display the main screen 70 shown in FIG. 6.

When the information transfer switch 71 is selected on the main screen 70 by an operator, the CPU 58 causes the patient-data input screen 72 shown in FIG. 7 to be displayed.

At step S2, the CPU 58 receives patient data input on the patient-data input screen 72 by an operator through the keyboard switch 74. In this embodiment, "KONISHI", "26", "male", "gallbladder removal surgery" and "Jul. 23, 2002" are input to the name, age, sex, operation and date fields, respectively, on the patient-data input screen 72.

When the NEXT switch 75 is selected on the patient-data input screen 72 by an operator, the CPU 58 causes the information-to-be-recorded select screen 76 shown in FIG. 8 to be displayed.

At step S3, on the information-to-be-recorded select screen 76, the CPU 58 receives the operator's selection of the function for registration in the hospital network 44. According to this embodiment, when the still-image switch 77 is selected on the information-to-be-recorded select screen 76 by an operator in order to store a still image, for example, the information-to-be-recorded select screen 80 for still images shown in FIG. 9 is displayed.

At step S4, on the information-to-be-recorded select screen 80, the CPU 58 receives the operator's selection of the still image to be registered with the recording device of the server 47 connecting to the hospital network 44. According to this embodiment, when a still image 1 is selected on the information-to-be-recorded select screen 80, for example, the still-image checking screen 81 for the still image 1 shown in FIG. 10 is displayed.

At step S5, when the still image to be registered is checked by an operator and the NEXT switch 83 is selected on the still-image checking screen 81, the CPU 58 causes the information add screen 85 shown in FIG. 11 to be displayed.

At step S6, on the information add screen 85, the CPU 58 receives the selection by an operator on whether the information of the anesthesia-apparatus related system 48 is added to registered information or not.

When the YES switch 86 is selected by an operator on the information add screen 85, the CPU 58 causes the additional function select screen 88 shown in FIG. 12 to be displayed. On the other hand, when the NO switch 87 is selected by an operator on the information add screen 85 on the centralized operation panel 67, the processing goes to step S9.

At step S7, on the additional function select screen 88, the CPU 58 receives the selection, by an operator, of a function to be added. According to this embodiment, the heart rate switch 89 and the blood pressure switch 90 are selected, for example, on the additional function select screen 88, and data of the two switches 89 and 90 are added.

When the NEXT switch 92 is selected by an operator on the additional function select screen 88, the CPU 58 causes the information-to-be-registered checking screen 93 shown in FIG. 13 to be displayed.

At step S8, on the information-to-be-registered checking screen 93, the CPU 58 receives the selection, by an operator, of whether the selected information is to be registered with the storage device of the server 47 connecting to the hospital network 44 or not.

When the selected information is registered with the hospital network 44 on the information-to-be-registered checking screen 93, the CPU 58 receives the selection of the register switch 97 by an operator. Then, the processing goes to step S9. At step S9, the CPU 58 registers the selected still image, patient data, heart rate and blood pressure with the storage device of the server 47 connecting to the hospital network 44.

According to this embodiment, data of the endoscopic system 1 is transferred to the hospital network 44 through the anesthesia-apparatus related system 48 so that data to be used in an operating room can be transferred through one path. Thus, the construction is simplified, and the ease of use can be improved.

[Second Embodiment]

Since a second embodiment is almost the same as the first embodiment, only differences therebetween will be described. The same reference numerals will be given to the same components, the description of which will be omitted hereinafter.

Figure 15:
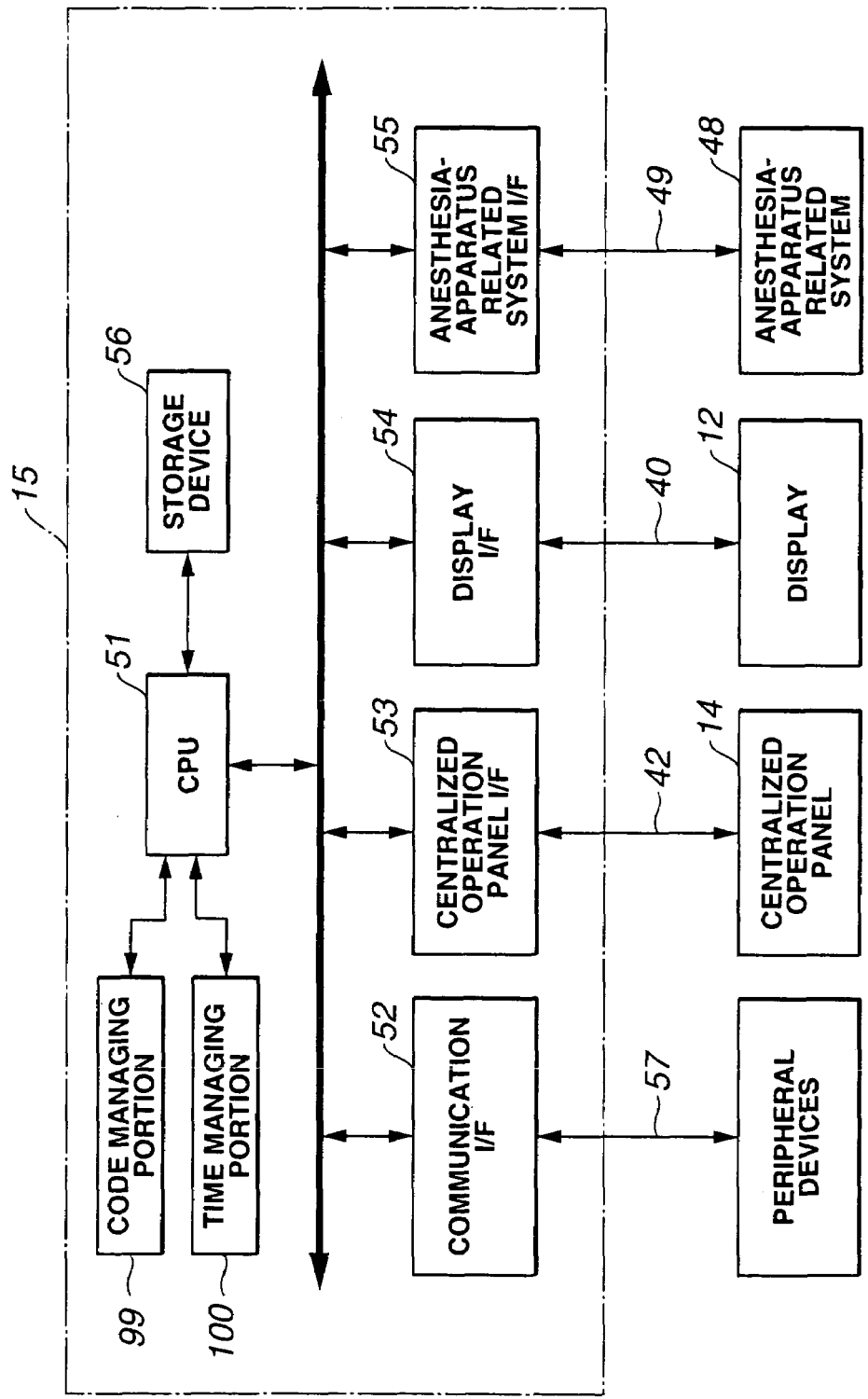
FIG. 15 is a block diagram showing a construction of a system controller according to a second embodiment of the present invention.

FIG. 15 shows an internal construction of a system controller 15.

The system controller 15 has a code managing portion 99 and a time managing portion 100, which are connected to the CPU 51 respectively, in addition to the construction according to the first embodiment.

FIG. 16 shows an internal construction of an anesthesia-apparatus related system 48.

The anesthesia-apparatus related system 48 has an abnormality detecting sensor 101, a code managing portion 102 and a time managing portion 103, which are all connected to the CPU 58, in addition to the construction according to the first embodiment.

FIGS. 17 to 24 show different kinds of operation screens on a centralized operation panel 67 of the anesthesia-apparatus related system 48.

Figure 17:
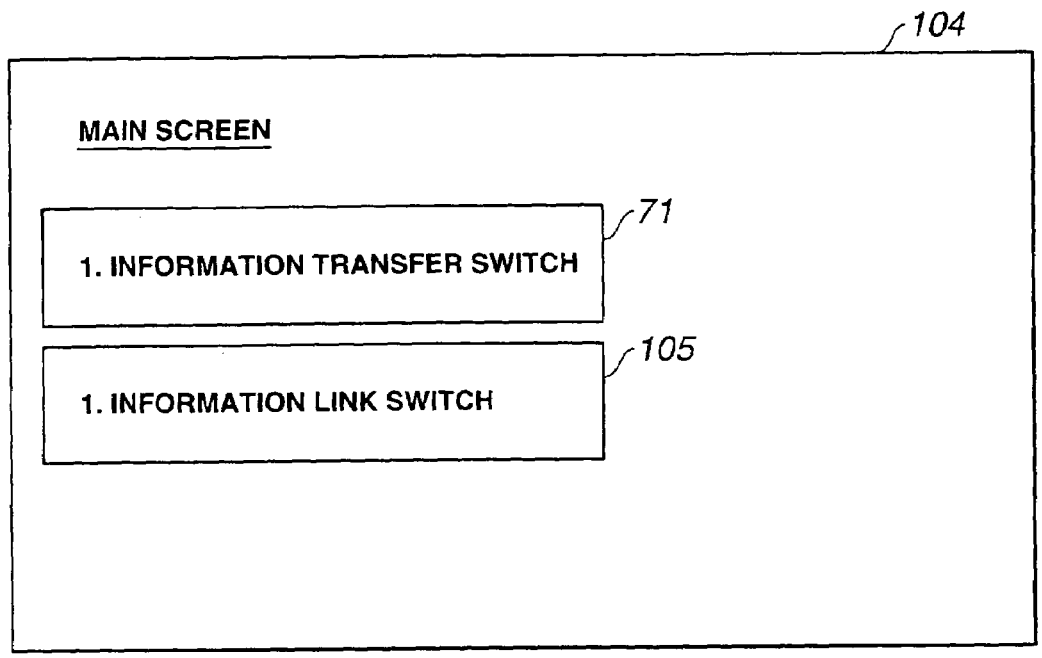
FIG. 17 is a diagram showing a first operation screen to be displayed on a centralized operation panel of the anesthesia-apparatus related system in FIG. 16.

FIG. 17 shows a main screen 94 on the centralized operation panel 67 of the anesthesia-apparatus related system 48. The main screen 94 has an information link switch 105. When the information link switch 105 is selected on the main screen 94, the centralized operation panel 67 displays the patient-data input screen 72 shown in FIG. 7.

Figure 18:
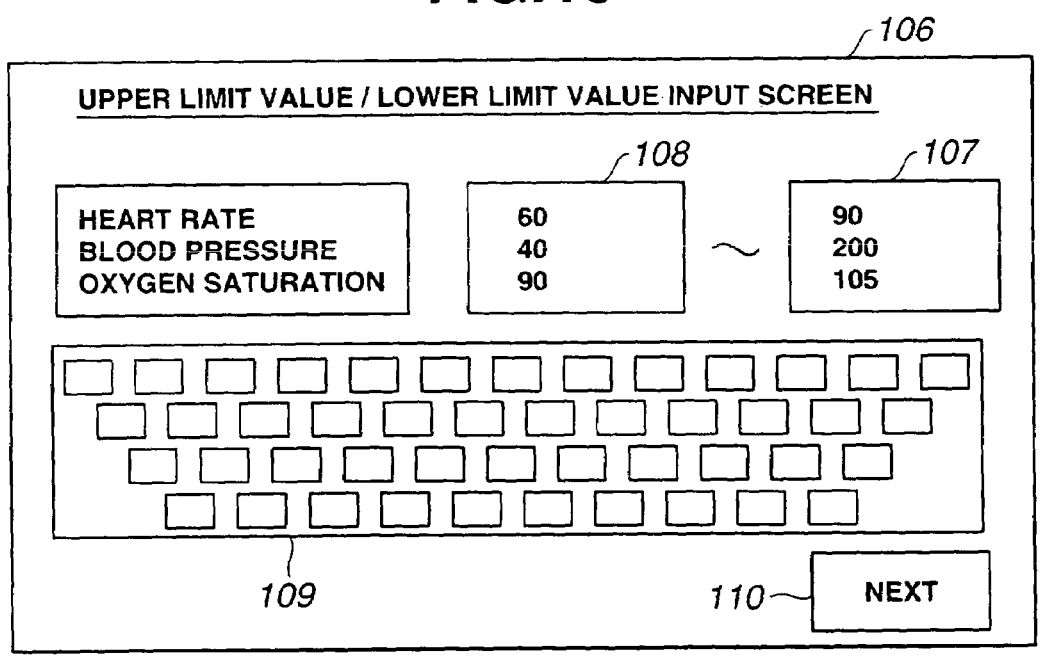
FIG. 18 is a diagram showing a second operation screen to be displayed on the centralized operation panel of the anesthesia-apparatus related system in FIG. 16.

FIG. 18 shows an upper limit value/lower limit value input screen 106. The upper limit value/lower limit value input screen 106 has an upper limit input field 107, a lower limit value input field 108, a keyboard switch 109 and a NEXT switch 110.

Upper limit and lower limit values of a heart rate, blood pressure and oxygen saturation are input on the upper limit value/lower limit value input screen 106 on the centralized operation panel 67 through the keyboard switch 109. When the NEXT switch 110 is selected on the upper limit value/lower limit value input screen 106, the centralized operation panel 67 displays a function-to-be-linked select screen 111 shown in FIG. 19.

Figure 19:
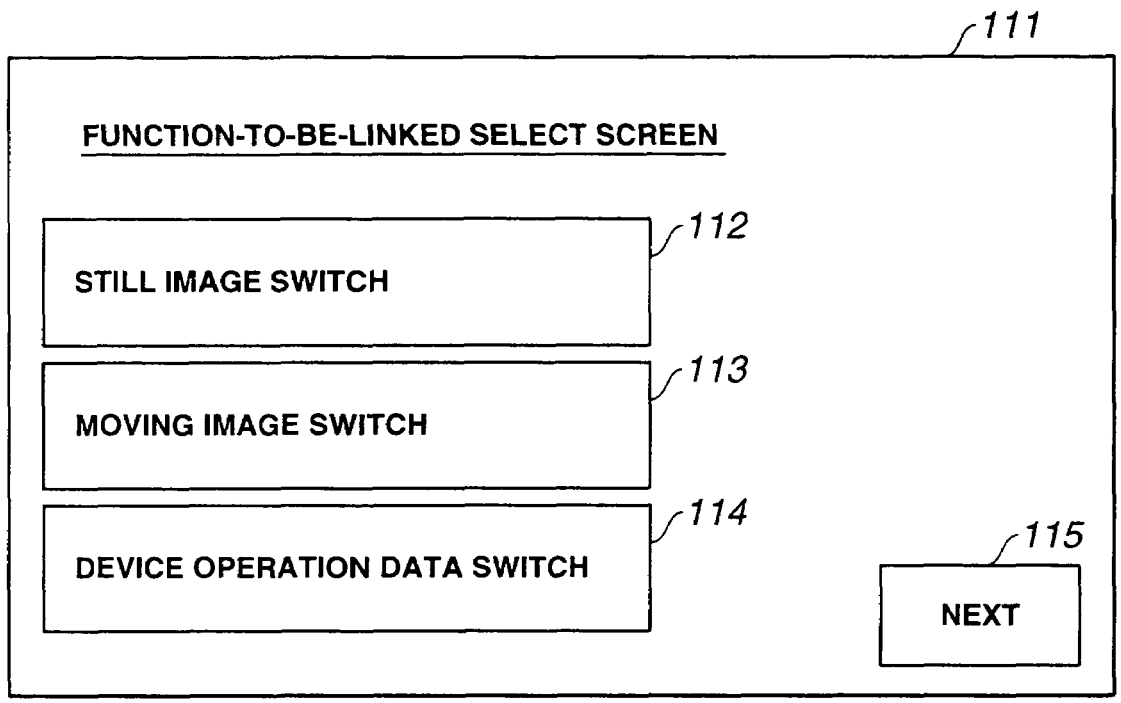
FIG. 19 is a diagram showing a third operation screen to be displayed on the centralized operation panel of the anesthesia-apparatus related system in FIG. 16.

FIG. 19 shows the function-to-be-linked select screen 111. The function-to-be-linked select screen 111 has a still image switch 112, a moving image switch 113, a device operational data switch 114 and a NEXT switch 115. When a function to be linked is selected on the function-to-be-linked select screen 111 on the centralized operation panel 67, a function for recording an abnormality if detected is set.

Figure 20:
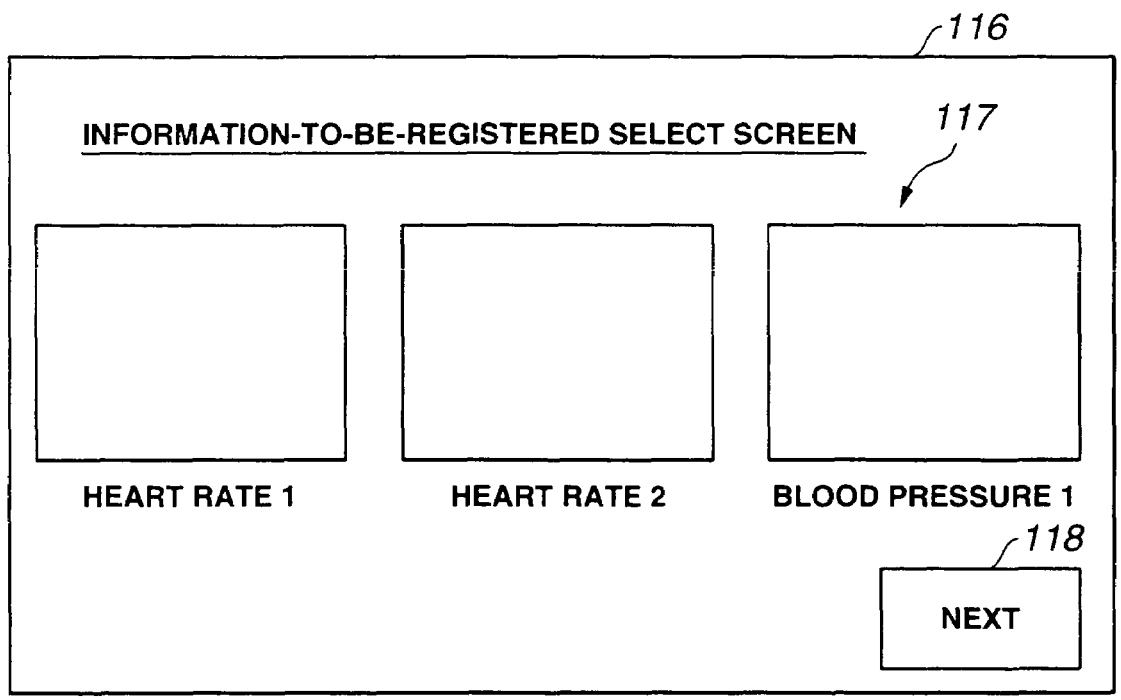
FIG. 20 is a diagram showing a fourth operation screen to be displayed on the centralized operation panel of the anesthesia-apparatus related system in FIG. 16.

FIG. 20 shows an information-to-be-registered select screen 116. The information-to-be-registered select screen 116 has an information-to-be-registered select switch 117 and a NEXT switch 118. When a function to be linked is selected on the information-to-be-registered select screen 116 on the centralized operation panel 67, a function for recording an abnormality, if detected, is set.

Figure 21:
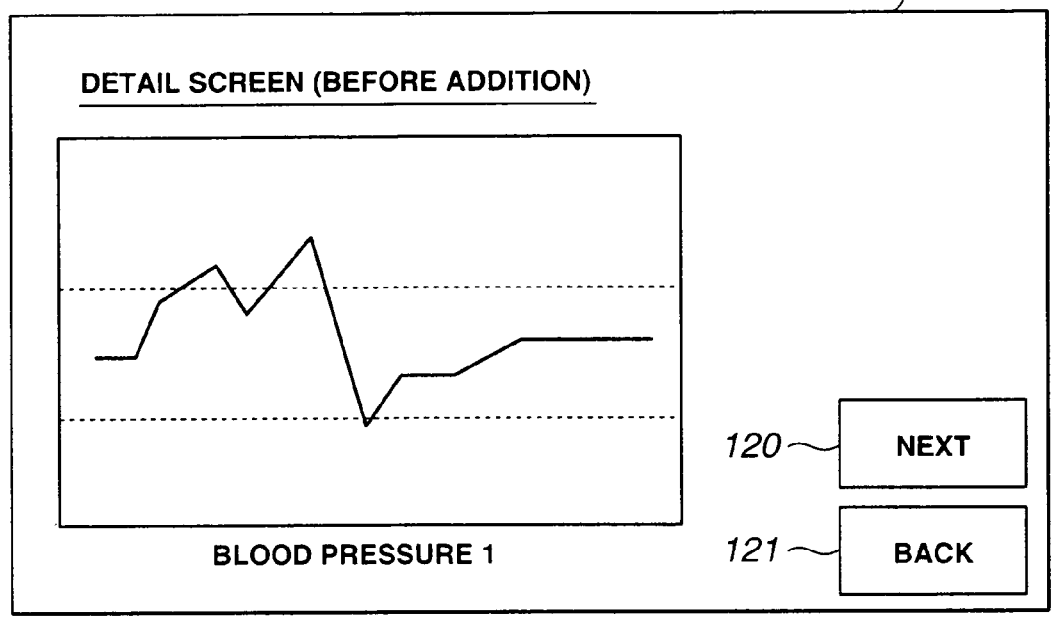
FIG. 21 is a diagram showing a fifth operation screen to be displayed on the centralized operation panel of the anesthesia-apparatus related system in FIG. 16.

When the NEXT switch 118 is selected on the information-to-be-registered select screen 116, the centralized operation panel 67 further displays a detail screen (before addition) 119 shown in FIG. 21.

FIG. 21 shows the detail screen (before addition) 119. The detail screen (before addition) 119 has a NEXT switch 120 and a BACK switch 121. When the NEXT switch 120 is selected on the detail screen (before addition) 119, the centralized operation panel 67 displays an information-to-be-added select screen 122 shown in FIG. 22.

When the BACK switch 121 is selected on the detail screen (before addition) 119, the centralized operation panel 67 displays the information-to-be-registered select screen 116 in FIG. 20 again.

Figure 22:
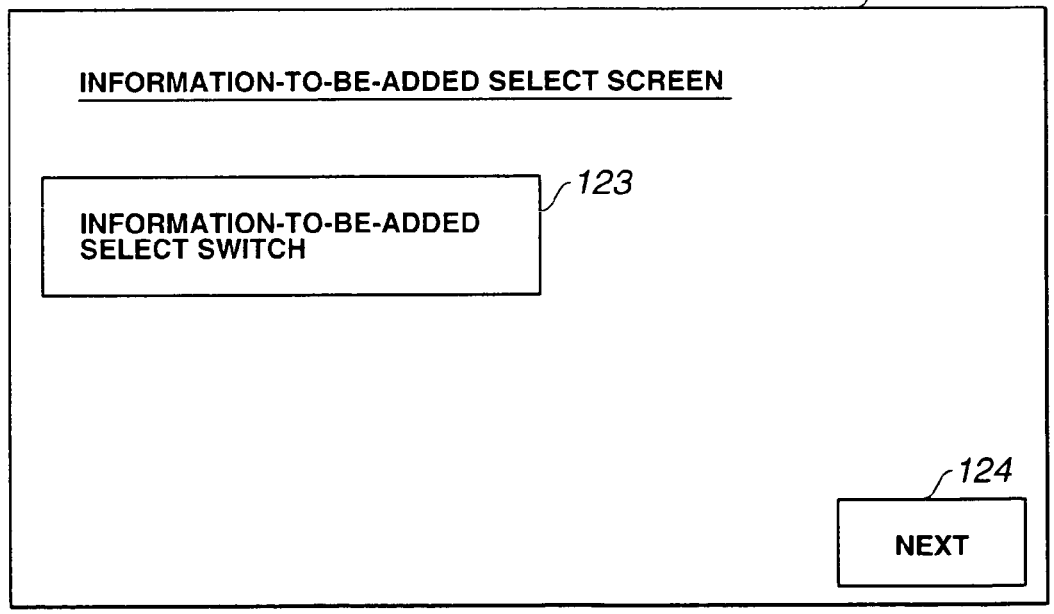
FIG. 22 is a diagram showing a sixth operation screen to be displayed on the centralized operation panel of the anesthesia-apparatus related system in FIG. 16.

FIG. 22 shows the information-to-be-added select screen 122. The information-to-be-added select screen 122 has an information-to-be-added select switch 123 and a NEXT switch 124. When information to be added is selected and the NEXT switch 124 is selected on the information-to-be-added select screen 122, the centralized operation panel 67 displays a detail screen (after addition) 125 shown in FIG. 23.

FIG. 23 shows the detail screen (after addition) 125. The detail screen (after addition) 125 has a registered information display area 126, a NEXT switch 127 and a BACK switch 128. When the NEXT switch 127 is selected on the detail screen (after addition) 125, the centralized operation panel 67 displays a network registration screen 129 shown in FIG. 24.

When the BACK switch 128 is selected on the detail screen (after addition) 125, the centralized operation panel 67 displays the information-to-be-added select screen 122 in FIG. 22 again.

FIG. 24 shows the network registration screen 129. The network registration screen 129 has an YES switch 130 and a NO switch 131. When the YES switch 130 is selected on the network registration screen 129 on the centralized operation panel 67, information is registered with the recording device of a server 47 connected to a hospital network 44.

When the NO switch 131 is selected on the network registration screen 129, the centralized operation panel 67 displays the detail screen (after addition) 125 in FIG. 23 again.

FIGS. 25 and 26 show a method for storing data indicating an abnormal value and data held by the endoscopic system 1 at that time in the hospital network 44 in association when information in the anesthesia-apparatus related system 48 indicates the abnormal value.

At step S31, the CPU 58 of the anesthesia-apparatus related system 48 causes a main screen 104 shown in FIG. 17 to be displayed on the centralized operation panel 67. When the information link switch 105 is selected by an operator on the main screen 104, the CPU 58 causes a patient-data input screen 72 shown in FIG. 7 to be displayed.

At step S32, on the patient-data input screen 72, the CPU 58 receives patient data input by an operator from the keyboard switch 74. In this embodiment, "KONISHI", "26", "male", "gallbladder removal surgery" and "Jul. 23, 2002" are input to the name, age, sex, operation and date fields, respectively, on the patient-data input screen 72.

When the NEXT switch is selected on the patient-data input screen 72 by an operator, the CPU 58 causes the upper limit value/lower limit value input screen 106 shown in FIG. 18 to be displayed.

At step S33, the CPU 58 receives the upper limit value and lower limit value of information in the anesthesia-apparatus related system 48, which are input on the upper limit value/lower limit value input screen 106 by an operator. In this embodiment, the heart rate, blood pressure and oxygen saturation are set to 60 to 90 times/min., 40 to 200 mmHg and 90 to 105%, respectively, for example, on the upper limit value/lower limit value input screen 106.

When the NEXT switch 110 is selected on the upper limit value/lower limit value input screen 106 by an operator, the CPU 58 causes the function-to-be-linked select screen 111 shown in FIG. 19 to be displayed.

At step S34, the CPU 58 receives on the function-to-be-linked select screen 111, the selection, by an operator, of a function within the endoscopic system 1 for recording an abnormality, if detected, that is, a select function switch to be linked. According to this embodiment, the still image switch 112 is selected on the function-to-be-linked select screen 111.

When the NEXT switch 115 is selected on the function-to-be-linked select screen 111 by an operator, the CPU 58 goes to step S35. At step S35, the CPU 58 starts measuring information in the anesthesia-apparatus related system 48 and goes to step S36.

At step S36, the CPU 58 receives the determination, by an abnormality detecting sensor 101, on whether or not any abnormality has occurred in the information in the anesthesia-apparatus related system 48. According to this embodiment, when the abnormality detecting sensor 101 detects an abnormality, for example, when the blood pressure value is above 200 mmHg, the processing goes to step S37. When the abnormality detecting sensor 101 detects no abnormalities, the CPU 58 returns to step S35.

At step S37, when the abnormality detecting sensor 101 detects an abnormality, the CPU 58 files the data before and after the detection. According to this embodiment, data from five minutes before the occurrence of an abnormality to five minutes after the abnormality detection, for example, is stored in the storage device 66 as one file. Then, the processing goes to step S38.

At step S38, the CPU 58 causes the code managing portion 102 to assign a Warning code to a file recorded in the storage device 66. According to this embodiment, a Warning code 1 is assigned thereto, and the processing then goes to step S39.

At step S39, the CPU 58 sends the assigned Warning code 1 to the endoscopic system 1. Then, the processing goes to step S40. At step S40, the CPU 58 causes the CPU 51 of the endoscopic system 1 to receive the Warning code 1 and registers the Warning code 1 with the storage device 56. Then, the processing goes to step S41.

At step S41, the CPU 58 starts a function to be selected as a function to be linked. According to this embodiment, a still image is shot and is recorded in the storage device 56 of the endoscopic system 1. Then, the Warning code 1 transmitted from the anesthesia-apparatus related system 48 is assigned to the recorded information. The code managing portion 99 also assigns the time when the still image is shot by using the time managing portion 100 to the recorded information. Then, the processing goes to step S42.

At step S42, the CPU 58 determines whether or not a predetermined period of time has passed from the record of the function to be selected as a function to be linked. If the predetermined period of time has passed, the CPU 58 goes to step S41. If the predetermined period of time has not passed, the CPU 58 goes to step S43.

At step S43, the CPU 58 checks whether or not a predetermined period of time has passed from the detection of an abnormality. If the predetermined period of time has passed, the CPU 58 goes to step S44. If the predetermined period of time has not passed, the CPU 58 returns to step S42.

At step S44, the CPU 58 causes the information-to-be-registered select screen 116 shown in FIG. 20 to be displayed. When the information to be registered with the recording device of the server 47 connecting to the hospital network 44 is selected by an operator on the information-to-be-registered select screen 116 and the NEXT switch 118 is then selected, the CPU 58 causes the detail screen (before addition) 119 shown in FIG. 21 to be displayed. In this embodiment, a blood pressure 1, for example, is selected.

At step S45, the CPU 58 causes the detail of blood-pressure information to be registered to be displayed on the detail screen (before addition) 119. When the displayed information is registered with the recording device of the server 47 connected to the hospital network 44, the CPU 58 causes the information-to-be-added select screen 122 shown in FIG. 22 to be displayed on the detail screen (before addition) 119 in response to the selection of the NEXT switch 120 by an operator.

At step S46, when the information to be added is selected on the information-to-be-added select screen 122 and when the information-to-be-added select switch 123 is selected by an operator and the NEXT switch 124 is selected, the CPU 58 causes the detail screen (after addition) 125 shown in FIG. 23 to be displayed and goes to step S47.

When the NEXT switch 124 is selected by an operator on the information-to-be-added select screen 122 instead of the selection of the information-to-be-added select switch 123, the CPU 58 goes to step S48. At step S47, the CPU 58 adds to the blood pressure information and displays on the information-to-be-added select screen 122 the still image having the same Warning code as that of the blood pressure 1.

When the displayed information is to be registered with the hospital network 44 on the information-to-be-added select screen 122, the CPU 58 goes to step S48 in response to the selection of the NEXT switch 127 by an operator. On the other hand, when the BACK switch 128 is selected by an operator on the information-to-be-added select screen 122, the CPU 58 returns to step S46. At step S48, the CPU 58 registers the selected information with the recording device of the server 47 connected to the hospital network 44.

According to the second embodiment, in addition to the advantages of the first embodiment, an abnormal condition and information held by an endoscopic system at that time can be associated and be recorded chronologically. Thus, the labor after an operation can be largely reduced.

The present invention is not limited to the above-described embodiments, and various changes, modifications and the like thereof could be made without changing the principle of the present invention.

Having described the preferred embodiments of the invention referring to the accompanying drawing, it should be understood that the present invention is not limited to those precise embodiments and various changes and modification thereof could be made by one skilled in the art without departing from the spirit or scope of the invention as defined in the appended claims.

What is claimed is:

1. An endoscopic surgical system, comprising;
    an endoscopic system provided in an operating room and usable with an anesthesia-apparatus related system connected to a communication portion, said anesthesia-apparatus related system including an anesthesia administering apparatus for administering anesthesia to a patient;
    a transceiver provided in the anesthesia-apparatus related system, which can send and receive information; and
    an information creating portion for creating combined anesthesia-endoscopic image information by associating anesthesia information sent from the anesthesia-apparatus related system through the transceiver and endoscopic image information detected in the endoscopic system with a same patient, the information creating portion comprising:
    an information transfer select portion for providing a user transfer selection interface on a display screen for selecting whether or not the endoscopic image information is transferred to a recording device provided in a server connected to a hospital network;
    an information-to-be-recorded select portion for providing a user recording selection interface on the display screen for selecting the information of the anesthesia-apparatus related system to be added to the transferred endoscopic image information;
    an information-to-be-recorded checking portion for providing a user checking interface on the display screen for checking the information of the anesthesia-apparatus related system, which is selected in the information-to-be-recorded select portion; and
    an information-to-be-recorded adding portion for registering the information of the anesthesia-apparatus related system, which is checked in the information-to-be-recorded checking portion, with the recording device of the server connecting to the hospital network.

2. An endoscopic surgical system according to claim 1, further comprising:
    the anesthesia-apparatus related system having an anesthesia information recording portion for chronologically and sequentially recording anesthesia related information, which is the anesthesia information related to anesthesia in an operation;
    the endoscopic system having an image recording portion for chronologically and sequentially recording an operated-part image information, which is the endoscopic image information of the patient; and
    the information creating portion having an image-read-out control portion provided in the anesthesia apparatus related system for reading out and outputting to the communication portion operated-part image information recorded in the image recording portion based on time information communicated from the anesthesia-apparatus related system by the communication portion; and
    a recording control portion provided in the anesthesia-apparatus related system for controlling the anesthesia information recording portion so that the operated-part image information sent from the endoscopic system to the anesthesia-apparatus related system through the communication portion can be associated with the anesthesia related information of a same patient and can be recorded as the combined anesthesia-endoscopic image information.

3. An endoscopic surgical system according to claim 1, wherein the anesthesia-apparatus related system is provided in each of multiple operating rooms separately and is connected to a hospital network managed by a server over the communication portion.

4. An endoscopic surgical system according to claim 3, wherein the information creating portion transfers information of the endoscopic system to the hospital network through the anesthesia-apparatus related system and stores the information in the server.

5. An endoscopic surgical system according to claim 3, wherein, a warning code is issued when an abnormality is detected in the anesthesia information, and based on the warning code, the information creating portion associates the anesthesia information with the endoscopic image information, the combined anesthesia-endoscopic image information being subsequently transferred to the hospital network and stored-in the server.

6. An endoscopic surgical system according to claim 1, further comprising:
    the anesthesia-apparatus related system having a heart rate measuring instrument, a sphygmomanometer, and an oxygen saturation measuring instrument;
    the information creating portion being a CPU; and
    the transceiver including a centralized operation panel interface, a network interface and an endoscopic system interface.

7. An endoscopic surgical system according to claim 1, wherein the information creating portion is a system controller provided in an operating room, and the system controller includes a CPU, a communication interface, a centralized operation panel interface, a display interface, an anesthesia-apparatus related system interface and a storage device.

8. An endoscopic surgical system according to claim 1, wherein the information creating portion has a patient information input portion for receiving inputs of patient information and adds information of the anesthesia-apparatus related system to patient information input though the patient information input portion.

9. An endoscopic surgical system according to claim 8, wherein the information creating portion comprises:
    the information-to-be-recorded select portion for selecting whether or not operated-part image information or device operational information recorded in a storage device is added to the recording device provided in the server connected to the hospital network;
    the information-to-be-recorded checking portion for checking the operated-part image information or device operational information selected by the information-to-be-recorded select portion; and
    the information-to-be-recorded adding portion for registering the operated-part image information or device operational information checked by the information-tobe-recorded checking portion with the recording device of the server connecting to the hospital network.

10. An endoscopic surgical system according to claim 9, wherein the device operational information is heart-rate, blood-pressure and oxygen-saturation information.

11. An endoscopic surgical system according to claim 8, wherein the information creating portion further comprises:
- an upper limit value/lower limit value input portion for being used to input an upper limit value and lower limit value of information of the anesthesia-apparatus related system;
- an abnormality detecting portion for detecting an abnormality of the anesthesia-apparatus related system based on the upper limit value and lower limit value input by the upper limit value/lower limit value input portion;
- a function-to-be-linked select portion for, when an abnormality of the anesthesia-apparatus related system is detected by the abnormality detecting portion, selecting a function within the endoscopic system to be recorded in connection with the abnormality of the anesthesia-apparatus related system;
- an abnormality recording portion for implementing a function within the endoscopic system selected in the function-to-be-linked select portion and recording the abnormality of the anesthesia-apparatus related system; and
- a filing portion for filing information before and after the detection of the abnormality recorded by the abnormality recording portion.

12. An endoscopic operation system according to claim 11, wherein:
- the information-to-be-recorded select portion selects whether or not the information before and after the abnormality detection filed by the filing portion is added to the hospital network;
- the information-to-be-recorded checking portion checks the information before and after the abnormality detection selected by the information-to-be-recorded select portion; and
- the information-to-be-recorded adding portion registers the information before and after the abnormality detection checked by the information-to-be-recorded checking portion with the hospital network.

13. An endoscopic surgical system according to claim 11, the information creating portion further comprising:
- a code managing portion for assigning a warning code to the information before and after the abnormality detection filed by the filing portion; and
- an abnormality registration portion for sending to the endoscopic system and registering with the endoscopic system the information before and after the abnormality detection having the warning code assigned by the code managing portion.

14. An endoscopic surgical system according to claim 11, wherein the information creating portion includes a determination portion for determining whether or not a predetermined period of time has passed from the record of the information before and after the abnormality detection in the abnormality recording portion and for determining whether or not a predetermined period of time has passed from the detection of an abnormality of the anesthesia-apparatus related system by the abnormality detecting portion.

15. An endoscopic surgical system, comprising:
- an anesthesia-apparatus related system having an anesthesia administering apparatus for administering anesthesia to a patient, and an anesthesia information recording portion for chronologically and sequentially recording anesthesia-related information relating to anesthesia in an operation;
- an endoscopic system having an image recording portion for chronologically and sequentially recording operated-part image information of a patient;
- an information creating portion provided in the anesthesia apparatus related system for creating combined anesthesia-endoscopic image information by associating anesthesia information sent from the anesthesia-apparatus related system and endoscopic image information detected in the endoscopic system with a same patient, the information creating portion comprising:
  - an information transfer select portion providing a user transfer selection interface on a display screen for selecting whether or not information of the anesthesia-apparatus related system is transferred to a recording device provided in a sewer connecting to a hospital network;
  - an information-to-be-recorded select portion for providing a user recording selection interface on the display screen for selecting whether or not information of the anesthesia-apparatus related system is added to the recording device of the server connecting
  - an information-to-be-recorded checking portion for providing a user checking interface on the display screen for checking the information of the anesthesia-apparatus related system, which is selected in the information-to-be-recorded select portion; and
  - an information-to-be-recorded adding portion for registering the information of the anesthesia-apparatus related system, which is checked in the information-to-be-recorded checking portion, with the recording device of the server connected to the hospital network;
- a communication portion for communicating between the anesthesia-apparatus related system and the endoscopic system;
- an image-read-out control portion provided in the endoscopic system for reading out and outputting to the communication portion the operated-part image information recorded in the image recording portion based on time information communicated from the anesthesia-apparatus related system to the endoscopic system by the communication portion; and
- a recording control portion provided in the anesthesia-apparatus related system for controlling the anesthesia information recording portion to record the operated-part image information sent from the endoscopic system to the anesthesia-apparatus related system through the communication portion under the control of the image-read-out control portion in connection with the anesthesia-related information of a same patient.

16. An endoscopic surgical system, comprising:
- an information creating portion provided in an anesthesia apparatus related system for creating combined anesthesia-endoscopic image information by associating anesthesia information sent from the anesthesia-apparatus related system and endoscopic image information detected in the endoscopic system with a same patient, said anesthesia apparatus related system including an anesthesia administering apparatus for administering anesthesia to a patient, the information creating portion comprising:
  - an information-to-be-recorded select portion for providing a user recording selection interface on a display screen for selecting whether or not the information before and after the abnormality detection, which is filed in the filing portion, is registered to information in a recording device provided in a server connected to a hospital network;

an information-to-be-recorded checking portion for providing a user checking interface on a display screen for checking the information before and after the abnormality detection, which is selected in the information-to-be-recorded select portion; and an information-to-be-recorded adding portion for registering the information before and after the abnormality detection, which is checked in the information-to-be-recorded checking portion, with the recording device of the server connected to the hospital network;

an upper limit value/lower limit value input portion for receiving inputs of an upper limit value and lower limit value of information of the anesthesia-apparatus related system;

an abnormality detecting portion for detecting an abnormality of the anesthesia-apparatus related system based on the upper limit value and lower limit value, which are input in the upper limit value/lower limit value input portion;

a function-to-be-linked select portion for, when an abnormality of the anesthesia-apparatus related system is detected by the abnormality detecting portion, selecting a function in the endoscopic system to be recorded in connection with the abnormality of the anesthesia-apparatus related system;

an abnormality recording portion for implementing the function in the endoscopic system, which is selected in the function-to-be-linked select portion, and recording the abnormality of the anesthesia-apparatus related system; and a filing portion for filing the information before and after the detection of the abnormality, which is recorded by the abnormality recording portion.

* * * * *

UNITED STATES PATENT AND TRADEMARK OFFICE
CERTIFICATE OF CORRECTION

PATENT NO. : 7,413,541 B2 Page 1 of 1
APPLICATION NO. : 10/792240
DATED : August 19, 2008
INVENTOR(S) : Sumihito Konishi It is certified that error appears in the above-identified patent and that said Letters Patent is hereby corrected as shown below:

Column 14, Claim 8, Line 53:

"though" should read -- through --

Column 16, Claim 15, Line 18:

"sewer" should read -- server --

Signed and Sealed this

Second Day of December, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,413,541 B2 | Page 1 of 1 |
| APPLICATION NO. | : 10/792240 | |
| DATED | : August 19, 2008 | |
| INVENTOR(S) | : Sumihito Konishi | |

It is certified that error appears in the above-identified patent and that said Letters Patent is hereby corrected as shown below:

Column 14, Claim 8, Line 52:

"though" should read -- through --

Column 16, Claim 15, Line 18:

"sewer" should read -- server --

This certificate supersedes the Certificate of Correction issued December 2, 2008.

Signed and Sealed this

Third Day of August, 2010

David J. Kappos
*Director of the United States Patent and Trademark Office*